United States Patent
Ahn et al.

(10) Patent No.: US 11,739,223 B2
(45) Date of Patent: Aug. 29, 2023

(54) SURFACE PRIMER COMPOSITIONS AND METHODS OF USE

(71) Applicant: Envista, Brea, CA (US)

(72) Inventors: Byung Jun Ahn, Goleta, CA (US); Bruce H. Lipshutz, Santa Barbara, CA (US); Sam L. Nguyen, Saratoga, CA (US)

(73) Assignee: ENVISTA, Brea, CA (US)

( * ) Notice: Subject to any disclaimer, the term of this patent is extended or adjusted under 35 U.S.C. 154(b) by 0 days.

(21) Appl. No.: 17/740,350

(22) Filed: May 10, 2022

(65) Prior Publication Data
US 2023/0103027 A1 Mar. 30, 2023

Related U.S. Application Data

(62) Division of application No. 16/877,058, filed on May 18, 2020, now Pat. No. 11,352,512, which is a division of application No. 15/417,825, filed on Jan. 27, 2017, now Pat. No. 10,696,698.

(60) Provisional application No. 62/360,677, filed on Jul. 11, 2016, provisional application No. 62/309,156, filed on Mar. 16, 2016, provisional application No. 62/288,195, filed on Jan. 28, 2016.

(51) Int. Cl.

| | | |
|---|---|---|
| C09D 7/63 | (2018.01) | |
| C09D 5/00 | (2006.01) | |
| A61K 6/65 | (2020.01) | |
| A61K 6/20 | (2020.01) | |
| A61K 6/62 | (2020.01) | |
| A61K 6/78 | (2020.01) | |
| B05D 3/00 | (2006.01) | |
| B05D 3/10 | (2006.01) | |
| C07C 69/01 | (2006.01) | |
| C07C 205/42 | (2006.01) | |
| C07C 205/43 | (2006.01) | |
| C07C 235/06 | (2006.01) | |
| C07C 235/20 | (2006.01) | |
| C07C 271/16 | (2006.01) | |
| C07D 217/16 | (2006.01) | |
| C07F 7/08 | (2006.01) | |
| C07F 9/12 | (2006.01) | |
| C07F 9/62 | (2006.01) | |
| C08K 5/107 | (2006.01) | |
| C08K 5/13 | (2006.01) | |

(52) U.S. Cl.
CPC .............. *C09D 5/002* (2013.01); *A61K 6/20* (2020.01); *A61K 6/62* (2020.01); *A61K 6/65* (2020.01); *A61K 6/78* (2020.01); *B05D 3/002* (2013.01); *B05D 3/10* (2013.01); *B05D 3/107* (2013.01); *C07C 69/01* (2013.01); *C07C 205/42* (2013.01); *C07C 205/43* (2013.01); *C07C 235/06* (2013.01); *C07C 235/20* (2013.01); *C07C 271/16* (2013.01); *C07D 217/16* (2013.01); *C07F 7/0896* (2013.01); *C07F 9/12* (2013.01); *C07F 9/62* (2013.01); *C09D 7/63* (2018.01); *C08K 5/107* (2013.01); *C08K 5/13* (2013.01)

(58) Field of Classification Search
CPC .......... B05D 3/002; C08K 5/107; C08K 5/13
See application file for complete search history.

(56) References Cited

U.S. PATENT DOCUMENTS

| 4,327,022 | A | 4/1982 | Bailey |
| 4,500,601 | A | 2/1985 | Whitcomb |
| 4,954,659 | A | 9/1990 | Parkhurst et al. |
| 5,925,690 | A * | 7/1999 | Fuchigami ............... A61K 6/76 526/318.2 |
| 2013/0310591 | A1 | 11/2013 | Yoshioka et al. |

FOREIGN PATENT DOCUMENTS

| EP | 0712622 | 5/1996 |
| EP | 2924043 | 9/2015 |
| KR | 101458058 | 11/2014 |

OTHER PUBLICATIONS

B. Kollbe Ahn et al, High-Performance Mussel-Adhesives of Reduced Complexity, Nature Communications, Oct. 19, 2015, p. 1-7, Macmillan Publishers Limited.

* cited by examiner

*Primary Examiner* — Nathan T Leong
(74) *Attorney, Agent, or Firm* — Sam L. Nguyen; HDC IP Law, LLP

(57) ABSTRACT

In one embodiment, the present application discloses a surface binding compound of the Formula I or Formula II:

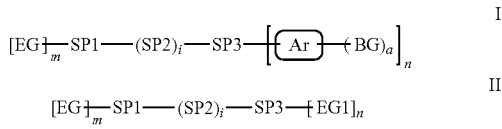

wherein the variables EG, EG1, SP1, SP2, SP3, Ar and BG are as defined herein. In another embodiment, the application discloses a method for forming a coating on a surface of a substrate using the surface binding compound of the Formula I or Formula II.

10 Claims, No Drawings

SURFACE PRIMER COMPOSITIONS AND METHODS OF USE

RELATED APPLICATIONS

This application is a Divisional of U.S. application Ser. No. 16/877,058 filed on May 18, 2020 and issued as U.S. Pat. No. 11,352,512, which is a Divisional of U.S. application Ser. No. 15/417,825 filed on Jan. 27, 2017 and issued as U.S. Pat. No. 10,696,698 on Jun. 30, 2020, which claims the benefit of U.S. Provisional Application No. 62/288,195 filed Jan. 28, 2016, U.S. Provisional Application No. 62/309,156 filed Mar. 16, 2016, and U.S. Provisional Application No. 62/360,677 filed Jul. 11, 2016, the disclosures of which are incorporated herein in their entirety.

BACKGROUND

Strong bidentate bonding, such as hydrogen bonding with catecholic groups, chelation and metal-oxygen coordination of the catechols and their applications as primers containing a catechol functional group are known in the art. These catecholic compounds form strong hydrogen bonds and function as chelators with different minerals and metal oxide surfaces.

SUMMARY OF THE INVENTION

In one embodiment, the present application discloses a surface binding compounds of the Formula I and Formula II:

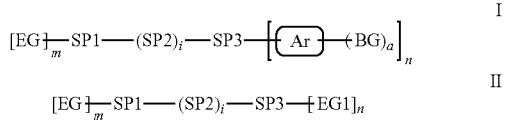

wherein the variables EG, EG1, SP1, SP2, SP3, Ar and BG are as defined herein. In another embodiment, the application discloses a method for using the compounds, including forming a coating on a surface of a substrate using the surface-binding compounds.

DETAILED DESCRIPTION OF THE INVENTION

In one embodiment, the present application discloses novel, structurally defined small molecule compounds as primers and adhesives for medical, dental and electronic applications. In one embodiment, the present application discloses primers, including polyhydroxy aromatic compounds, such as tri-, tetra- and penta-hydroxy benzene, polycyclic hydrocarbons (e.g., naphthalene, anthracene, etc.), aryls, heteroaryl, indole and imidazole moieties and their derivatives, that may form bonds, such as hydrogen bonds and/or attachments via chelation or coordination on to a material surface, such as a mineral, metal or oxide-containing surface of a material. In one aspect, these head moieties of the compounds adhere/adsorb onto mineral and metal oxide surfaces and generate secondary surfaces to interact (or crosslink) with bulk adhesive, resins or co-polymer surfaces to enhance performance of bonding between minerals, metals and metal oxide containing surfaces. Non-exclusive material surfaces include adhesives, cements, resins, paints, inks, proteins etc. . . .

Some embodiments of the current invention are discussed in detail below. In describing embodiments, specific terminology is employed for the sake of clarity. However, the present application is not intended to be limited to the specific terminology so selected. A person skilled in the relevant art will recognize that other equivalent components can be employed and other methods developed without departing from the broad concepts of the current invention. All references cited in this specification are incorporated by reference into this disclosure.

In one embodiment, the application discloses compounds comprising an aromatic group-containing surface primer. In one aspect, the surface primer contains an aromatic group. In another aspect, the compound comprises an aromatic group (or head group) attached to a functional end group (EG) through a spacer group. In another embodiment, the compounds undergo self-assembly onto a substrate, such as a mineral substrate or a metal oxide substrate. When applied to an oxide-containing surface, the aromatic group of the compound may self-assemble and form a bond, such as a hydrogen bond, onto the oxide-containing surface.

In another aspect, the compound forms a chelate, coordinating onto the metal surface of a substrate. The functional end group of the compound can form a secondary surface layer to interact/crosslink with bulk materials chemically, physiochemically or physically, via cross-linking, hydrogen bonding, oxide-metal coordination, electrostatic or hydrophobic interaction; and combinations thereof. A secondary surface can optionally be applied onto the primer. According to the present process, the secondary layer may be tunable by modifying the compound, including the functional end group, such as the aromatic group.

In one embodiment, the present application discloses a surface binding compound of the Formula I:

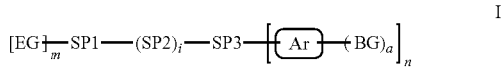

wherein:
each a is independently 1, 2, 3, 4 or 5;
m is 1, 2 or 3; n is 1, 2 or 3; i is 1, 2 or 3;
each EG is an end group independently selected from the group consisting of a $C_{1-12}$alkyl, $CH_2$=CH—, $CH_2$=$C(C_{1-3}$alkyl)-, $CH_2$=CHC(O)—, $CH_2$=$C(C_{1-3}$alkyl)C(O)—, $CH_2$=CHC(O)O—, $CH_2$=$C(C_{1-3}$alkyl)C(O)O—, $CH_2$=C(phenyl)C(O)O—, $CH_2$=$C(C_{1-3}$alkyl)S(O)$_n$O—, isocyanate, epoxy, oxetanyl, styrenyl, vinyl ether, (OH)Si(R)$_2$—, (OH)Si(R)$_2$(O)—, —Ar—(BG)$_a$, aryl, heteroaryl, —N$^+$R$_1$R$_2$R$_3$, —PO$_4^-$, —N$^+$R$_1$R$_2$R$_3$X$^-$, —PO$_4^-$Y$^+$ and —SO$_4^-$Y$^+$, wherein each R, R$_1$, R$_2$ and R$_3$ is independently H and $C_{1-3}$alkyl, or optionally substituted $C_{1-3}$alkyl, or wherein R$_1$, R$_2$ and R$_3$ are combined with N to form a heterocyclic compound, X$^-$ is Cl$^-$, Br$^-$ and I$^-$ and Y$^+$ is H$^+$ or N$^+$R$_1$R$_2$R$_3$;

each of SP1, SP2 and SP3 is a spacer independently selected from the group consisting of —O—, —C(O)—, —S—, —S(O)—, —S(O)$_2$—, —N—, —NH—, —NCH$_3$—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —NH(CH$_2$)$_2$NH—, —OC(O)—, —CO$_2$—, —NHCH$_2$CH$_2$C(O)—, —OCH$_2$CH$_2$C(O)—, —C(O)CH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$ $CH_2O)_pCH_2CH_2$—, —$CH_2CH_2$—$(CH_2CH_2O)_p$—, —OCH$(CH_2O$—$)_2$—, —$(CH_2)_q$—$N^+R_1R_2$—, —$(CH_2)_q$—$PO_4^-$, —$N^+R_1R_2$—, —$PO_4^-$, —$(CH_2)_q$—$N^+R_1R_2$—$X^-$, —$(CH_2)_q$—$PO_4^-Y^+$, —$N^+R_1R_2$—$X^-$, —$PO_4^-Y^+$—, —$SO_4^-Y^+$—, —O—$PO^-(O)O$—$(CH_2)_{2-4}$—$N^+(R_1R_2)$—, -(AA)$_r$-, aryl, cyclopentanyl, cyclohexanyl, unsubstituted phenylenyl and phenylenyl substituted by 1 or 2 substituents selected from the group consisting of halo, $CF_3$—, $CF_3O$—, $CH_3O$—, —C(O)OH, —C(O)O$C_{1-3}$alkyl, —C(O)$CH_3$, —CN, —$NH_2$, —OH, —$NHCH_3$, —$N(CH_3)_2$ and $C_{1-3}$alkyl, wherein each AA is independently an amino acid, p is 1-6, q is 1-6 and r is 1-6;

Ar is an aryl or heteroaryl group; and each BG is a bonding group independently selected from the group consisting of —OH, —Si(R)$_2$OH, —COOH, —SO$_3$H, —P(O)$_3$OH, —CONH$_2$, —CSNH$_2$, —CF$_3$, —CF$_2$CF$_3$, —OCF$_3$ and —OCF$_2$CF$_3$; provided that when —SP3 is —CH$_2$— or —C(O)—, then Ar—(BG)$_a$ is not 3,4-dihydroxyphenyl or 3,4-dicarboxyphenyl. In one variation of the compound, when Ar—(BG)$_a$ is 3,4-dihydroxyphenyl, then the group EG-SP1-SP2-Sp3- together is not selected from the group consisting of $C_{4-12}$alkyl-$N^+R_1R_2$—$(CH_2)_q$—$PO_4^-$-C$_3$alkyl- and aryl-C$_3$alkyl-$N^+R_1R_2$—$(CH_2)_q$—$PO_4^-$-C$_3$alkyl-, where q is 2 and $R_1$ and $R_2$ are both —CH$_3$; and when Ar—(BG)$_a$ is 3,4-dihydroxyphenyl, then the group EG-SP1-SP2-Sp3- together is not selected from the group consisting of $CH_2$=$CH_2CO_2$—$(CH_2)OC(O)$—$CH_2CH_2$— and $CH_2$=$CH_2CO_2$—$(CH_2)_{1-8}OC(O)$—$CH_2CH_2$—.

In another embodiment, the present application discloses a surface binding compound of the Formula II:

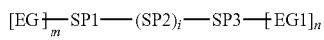

II wherein:

m is 1, 2 or 3; n is 1, 2 or 3; i is 1, 2 or 3;

each EG and EG1 is an end group independently selected from the group consisting of a $C_{1-12}$alkyl, $CH_2$=CH—, $CH_2$=C($C_{1-3}$alkyl)-, $CH_2$=CHC(O)—, $CH_2$=C($C_{1-3}$alkyl)C(O)—, $CH_2$=CHC(O)O—, $CH_2$=C($C_{1-3}$alkyl)C(O)O—, $CH_2$=C(phenyl)C(O)O—, $CH_2$=C($C_{1-3}$alkyl)S(O)$_n$O—, isocyanate, epoxy, oxetanyl, styrenyl, vinyl ether, (OH)Si(R)$_2$—, (OH)Si(R)$_2$(O)—, —Ar—(BG)$_a$, aryl, heteroaryl, —$N^+R_1R_2R_3$, —$PO_4^-$, —$N^+R_1R_2R_3X^-$, —$PO_4^-Y^+$ and —$SO_4^-Y^+$, wherein each R, $R_1$, $R_2$ and $R_3$ is independently H and $C_{1-3}$alkyl, or optionally substituted $C_{1-3}$alkyl, or wherein $R_1$, $R_2$ and $R_3$ are combined with N to form a heterocyclic compound, $X^-$ is $Cl^-$, $Br^-$ and $I^-$ and $Y^+$ is $H^+$ or $N^+R_1R_2R_3$;

each BG is a bonding group independently selected from the group consisting of —OH, —Si(R)$_2$OH, —COOH, —SO$_3$H, —P(O)$_3$OH, —CONH$_2$, —CSNH$_2$, —CF$_3$, —CF$_2$CF$_3$, —OCF$_3$ and —OCF$_2$CF$_3$, wherein each R is independently H and $C_{1-3}$alkyl;

each of SP1, SP2 and SP3 is a spacer independently selected from the group consisting of —O—, —C(O)—, —S—, —S(O)—, —S(O)$_2$—, —N—, —NH—, —NCH$_3$—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —NH(CH$_2$)$_2$NH—, —OC(O)—, —CO$_2$—, —NHCH$_2$CH$_2$C(O)—, —OCH$_2$CH$_2$C(O)—, —C(O)CH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$O)$_p$CH$_2$CH$_2$—, —CH$_2$CH$_2$—(CH$_2$CH$_2$O)$_p$—, —OCH(CH$_2$O—)$_2$—, —(CH$_2$)$_q$—$N^+R_1R_2$—, —(CH$_2$)$_q$—$PO_4^-$, —$N^+R_1R_2$—, —$PO_4^-$, —(CH$_2$)$_q$—$N^+R_1R_2$—$X^-$, —(CH$_2$)$_q$—$PO_4^-Y^+$, —$N^+R_1R_2$—$X^-$—, —$PO_4^-Y^+$—, —$SO_4^-Y^+$—, —O—PO$^-$(O)O—(CH$_2$)$_{2-4}$—$N^+(R_1R_2)$—, -(AA)$_r$-, aryl, cyclopentanyl, cyclohexanyl, unsubstituted phenylenyl and phenylenyl substituted by 1 or 2 substituents selected from the group consisting of halo, $CF_3$—, $CF_3O$—, $CH_3O$—, —C(O)OH, —C(O)O$C_{1-3}$alkyl, —C(O)$CH_3$, —CN, —$NH_2$, —OH, —$NHCH_3$, —$N(CH_3)_2$ and $C_{1-3}$alkyl, wherein each AA is independently an amino acid, p is 1-6, q is 1-6 and r is 1-6. In one variation, each R, $R_1$, $R_2$ and $R_3$ is independently $C_{1-3}$alkyl optionally substituted with —OH, —SH or —NH$_2$. In one variation, each R, $R_1$, $R_2$ and $R_3$ is independently selected from —CH$_3$ and —CH$_2$OH.

As provided herein and used conventionally in the art, for the compound of the Formula I, the —Ar-BG group may be referred to as the head group, and the -EG group may be referred to as the tail group of the self-assembled layer or self assembled monolayer (SAM). For the compound of the Formula II, the -EG groups may be the same (symmetric) or different (asymmetric) and may be referred to arbitrarily as the head or tail group of the self-assembled layer or self assembled monolayer (SAM).

As used herein, the formation of SAMs refers to the spontaneous formation of organic assemblies of the compound of the Formula I or Formula II on a surface by the adsorption of compounds from the solution by a process of synergistic intermolecular and/or intramolecular interactions.

In one variation of the compound of the Formula I, —Ar-BG is not a 3,4-dihydroxyphenyl group.

As defined herein, when each of SP1, SP2 and SP3 is independently a —N—, —C—, —C(O)N— or —NC(O)— group, these trivalent and tetravalent groups may be substituted and may form branched structures, leading up to various arrays, as represented by, e.g., dendrimeric species. For example, when SP1 is —N— or —C—, the compound of the Formula I (or Formula II) may form a branched structure at the nitrogen atom or carbon atom, respectively, as shown:

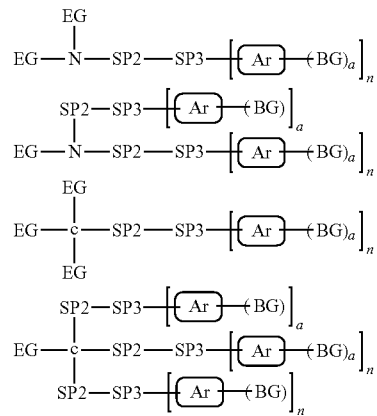

Similarly, branched structures may also be formed with SP1 and SP2, SP2 and SP3, or a combination of SP1, SP2 and SP3.

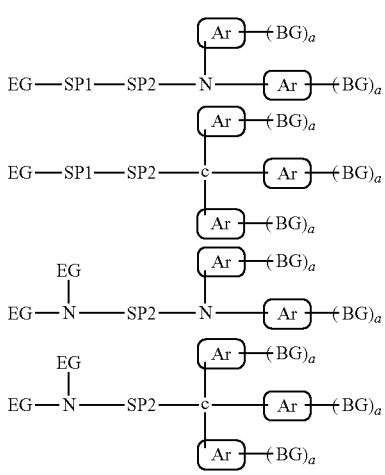

The dendrimer-like or branched structures disclosed above may also be similarly applicable for the compound of the Formula II.

As provided herein for example, a spacer designated or bonded as —C(O)NH— also includes the reversible (inverted) spacer that is bonded as —NHC(O)—.

In another variation, the SP1, SP2 and SP3 groups may be independently selected from:

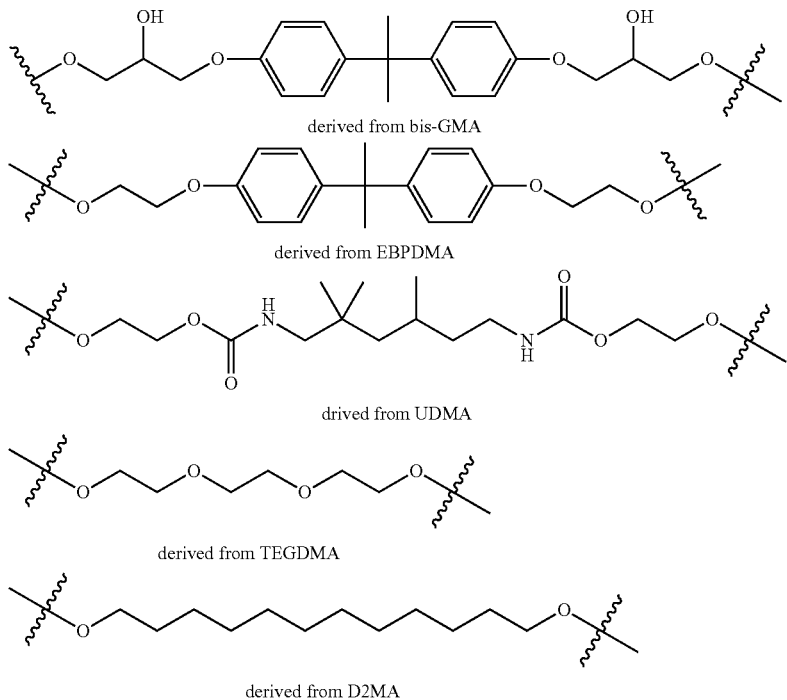

derived from bis-GMA derived from EBPDMA drived from UDMA derived from TEGDMA derived from D2MA In one aspect of the surface binding compound of the Formula I and Formula II, each EG is independently selected from the group consisting of a $C_{1-12}$alkyl, optionally substituted $C_{1-3}$alkyl, —N(CH$_3$)$_2$CH$_2$OH, —N(CH$_2$OH)$_2$CH$_3$, —N(CH$_2$OH)$_3$, —N(CH$_2$CH$_3$)$_2$CH$_2$CH$_2$OH, —N(CH$_2$CH$_2$OH)$_2$CH$_2$CH$_3$, —N(CH$_2$CH$_2$OH)$_3$, —N(CH$_3$)$_2$CH$_2$SH, —N(CH$_2$SH)$_2$CH$_3$, —N(CH$_2$SH)$_3$, —N(CH$_2$CH$_3$)$_2$CH$_2$CH$_2$SH, —N(CH$_2$CH$_2$SH)$_2$CH$_2$CH$_3$, —N(CH$_2$CH$_2$SH)$_3$, —N(CH$_3$)$_2$CH$_2$NH$_2$, —N(CH$_2$NH$_2$)$_2$CH$_3$, —N(CH$_2$NH$_2$)$_3$, —N(CH$_2$CH$_3$)$_2$CH$_2$CH$_2$NH$_2$, —N(CH$_2$CH$_2$NH$_2$)$_2$CH$_2$CH$_3$, —N(CH$_2$CH$_2$NH$_2$)$_3$, —N$^+$(CH$_3$)$_2$CH$_2$OH X$^-$, —N$^+$(CH$_2$OH)$_2$CH$_3$X$^-$, —N$^+$(CH$_2$OH)$_3$X$^-$, —N$^+$(CH$_2$CH$_3$)$_2$CH$_2$CH$_2$OH X$^-$, —N$^+$(CH$_2$CH$_2$OH)$_2$CH$_2$CH$_3$X$^-$, —N$^+$(CH$_2$CH$_2$OH)$_3$X$^-$, —N$^+$(CH$_3$)$_2$CH$_2$SH X$^-$, —N$^+$(CH$_2$SH)$_2$CH$_3$X$^-$, —N$^+$(CH$_2$SH)$_3$X$^-$, —N$^+$(CH$_2$CH$_3$)$_2$CH$_2$CH$_2$SH X$^-$, —N$^+$(CH$_2$CH$_2$SH)$_2$CH$_2$CH$_3$X$^-$, —N$^+$(CH$_2$CH$_2$SH)$_3$X$^-$, —N$^+$(CH$_3$)$_2$CH$_2$NH$_2$X$^-$, —N$^+$(CH$_2$NH$_2$)$_2$CH$_3$, X$^-$, —N$^+$(CH$_2$NH$_2$)$_3$X$^-$, —N$^+$(CH$_2$CH$_3$)$_2$CH$_2$CH$_2$NH$_2$X$^-$, —N$^+$(CH$_2$CH$_2$NH$_2$)$_2$CH$_2$CH$_3$X$^-$, —N$^+$(CH$_2$CH$_2$NH$_2$)$_3$X$^-$, CH$_2$=CHC(O)O—, CH$_2$=C(C$_{1-3}$alkyl)C(O)O—, CH$_2$=C(phenyl)C(O)O—, CH$_2$=CHS(O)$_n$O—, isocyanate, epoxy, oxetanyl, styrenyl, vinyl ether, —Ar—(BG)$_a$, phenyl and naphthyl or other polycyclic aromatics (e.g., anthracenyl, etc.); where X$^-$ is Cl$^-$, Br$^-$ and I$^-$. In one variation, each EG is independently selected from the group consisting of $C_1$alkyl, $C_3$alkyl, $C_6$alkyl, $C_{12}$alkyl, CH$_2$=C(CH$_3$)C(O)O—, CH$_2$=C(CH$_2$CH$_3$)C(O)O— and CH$_2$=C(CH$_2$CH$_2$CH$_3$)C(O)O—. In another variation, each EG is independently a $C_6$alkyl, $C_3$alkyl or a $C_1$alkyl or —CH$_3$. In another variation, each EG is independently selected from the group consisting of phenyl or naphthyl each optionally substituted by one or two functional groups selected from the group consisting of halo (F, Cl, Br, I), CF$_3$—, CF$_3$O—, CH$_3$O—, —C(O)OH, —C(O)OC$_{1-3}$alkyl, —C(O)CH$_3$, —CN, —NH$_2$, —OH, —NHCH$_3$, —N(CH$_3$)$_2$ and $C_{1-3}$alkyl.

In certain aspects, the EG tail may comprise of a polymerizable group, such as a mono-, di- or poly-acrylates and methacrylates (e.g., methyl acrylate, methyl methacrylate, ethyl(methyl)acrylate, isopropyl(methyl)acrylate, n-hexyl (methyl)acrylate, stearyl(methyl)acrylate, allyl(methyl) acrylate, glycerol di(methyl)acrylate, glycerol tri(methyl) acrylate, ethyleneglycol di(methyl)acrylate, diethyleneglycol di(methyl)acrylate, triethyleneglycol di(methyl)acrylate, 1,3-propanediol diacrylate, 1,3-propanediol dimethacrylate, trimethylolpropane tri(methyl)acrylate, 1,2,4-butanetriol tri(methyl)acrylate and 1,4-cyclohexanediol di(methyl)acrylate.

In another aspect of the surface binding compound, EG is independently selected from the group consisting of aryl, heteroaryl, imidazolyl, imidazolinium, indolinium, indolyl, $-N^+R_1R_2R_3$, $-PO_4^-$, $-N^+R_1R_2R_3X^-$, $-PO_4^-Y^+$, $-SO_4^-Y^+$, wherein each $R_1$, $R_2$ and $R_3$ is independently H and $C_{1-3}$alkyl and $C_{1-3}$alkyl substituted with 1, 2 or 3 —OH, 1, 2 or 3 —SH or 1, 2 or 3 —$NH_2$, $X^-$ is $Cl^-$, $Br^-$ and $I^-$ and $Y^+$ is $H^+$ or $-N^+R_1R_2R_3$. In another aspect of the surface binding compound, each of SP1, SP2 and SP3 is a spacer independently selected from the group consisting of $-(CH_2)_q-$, $-NH(CH_2)_2NH-$, $-NHCH_2CH_2C(O)-$, $-C(O)NHCH_2CH_2NH-$, $-NHCH_2C(O)-$, $-NHC(O)-$, $-C(O)N-$, $-NC(O)-$, $-C(O)NH-$, $-NCH_3C(O)-$, $-C(O)NCH_3-$, $-(CH_2CH_2O)_p-$, $-(CH_2CH_2O)_pCH_2CH_2-$, $-CH_2CH_2-(CH_2CH_2O)_p-$ and $-OCH(CH_2O-)_2-$. In one variation, the imidazolyl is an imidazolinium, and the indolyl is an indolinium and the counterion is a halide, sulfonate or phosphate.

In another aspect, each of SP1, SP2 and SP3 is a spacer independently selected from the group consisting of $-N^+R_1R_2-$, $-PO_4^-$, $-N^+R_1R_2X^--$, $-PO_4^-Y^+-$, $-SO_4^-Y^+-$, $-(CH_2)_q-N^+R_1R_2-$, $-(CH_2)_q-PO_4^-$, $-(CH_2)_q-N^+R_1R_2-X^--$, $-(CH_2)_q-PO_4^-Y^+-$ and $-O-PO^-(O)O-(CH_2)_{2-4}-N^+(R_1R_2)-$. In another aspect of the surface binding compound, SP1, SP2 and SP3 comprise of a group selected from $-CH_2CH_2-C(O)NHCH_2CH_2NH-C(O)NCH_3-$, $-NHC(O)-(CH_2CH_2O)_p-(CH_2)_q-$, $-(CH_2CH_2O)_pCH_2CH_2-C(O)NCH_3-(CH_2CH_2O)_pCH_2CH_2-$, $-NHCH_2CH_2C(O)-(CH_2)_q-PO_4^-$, $-PO_4^--(CH_2)_q-N^+R_1R_2X^--$, $-(CH_2CH_2O)_p-(CH_2)_q-PO_4^-$, $-N^+R_1R_2X^--(CH_2)_q-PO_4-$ and $-PO_4^--(CH_2CH_2O)_p-N^+R_1R_2X^--$.

In another aspect of the surface binding compound, Ar is an aryl group selected from the group consisting of:

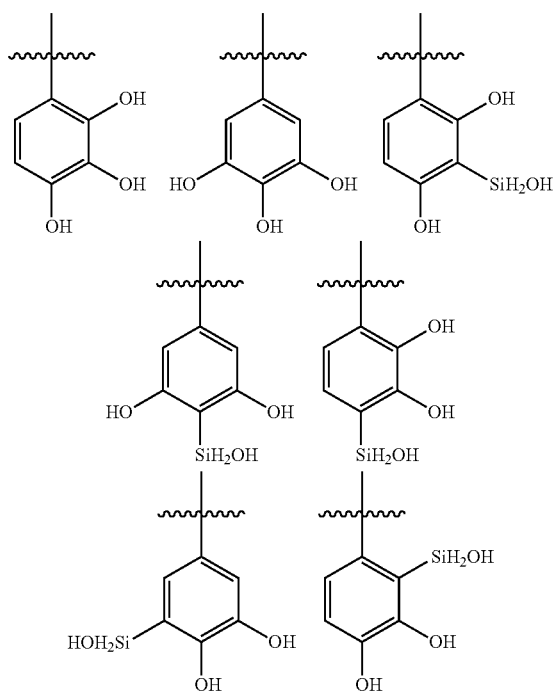

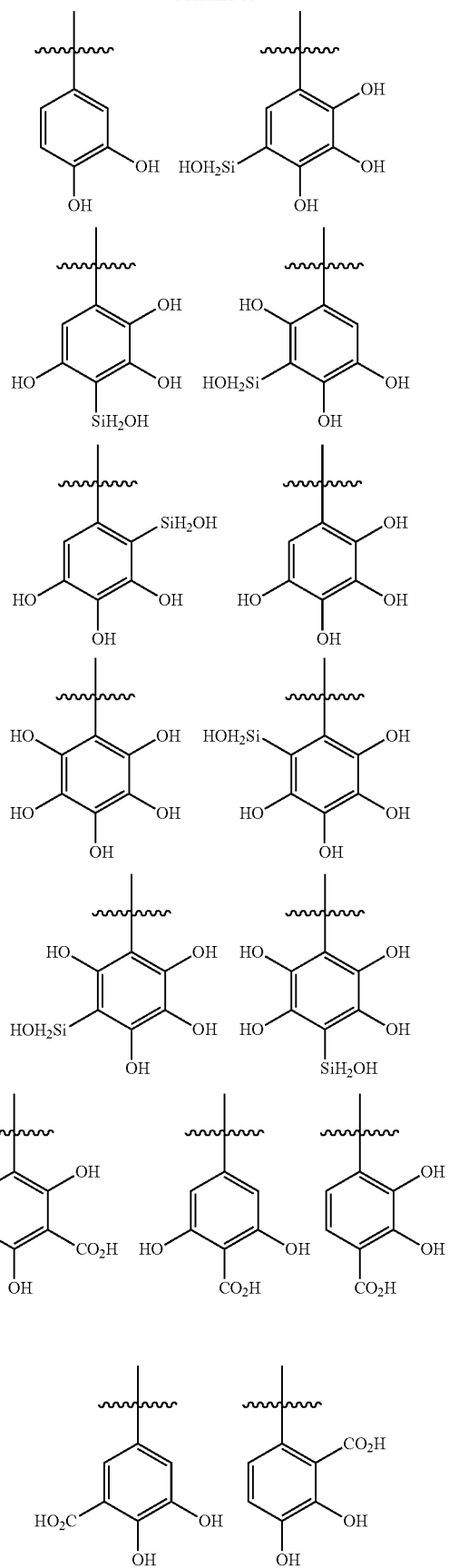

-continued
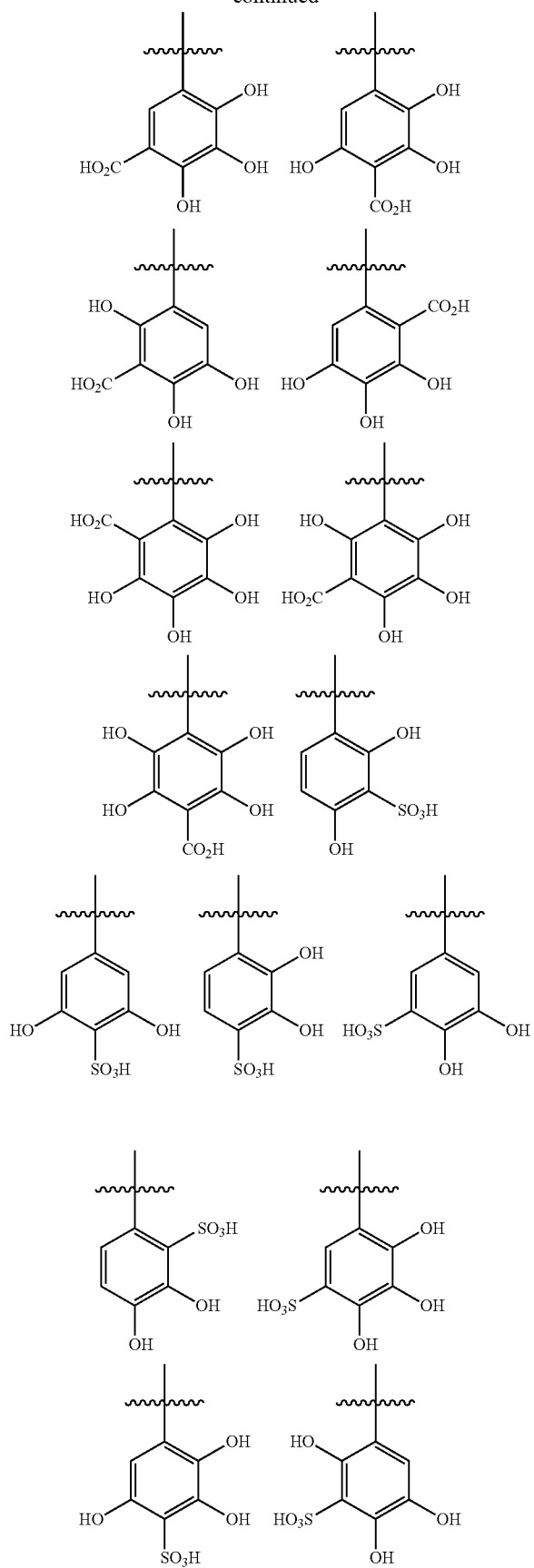
In another aspect of the above, Ar is an aryl group selected from the group consisting of:
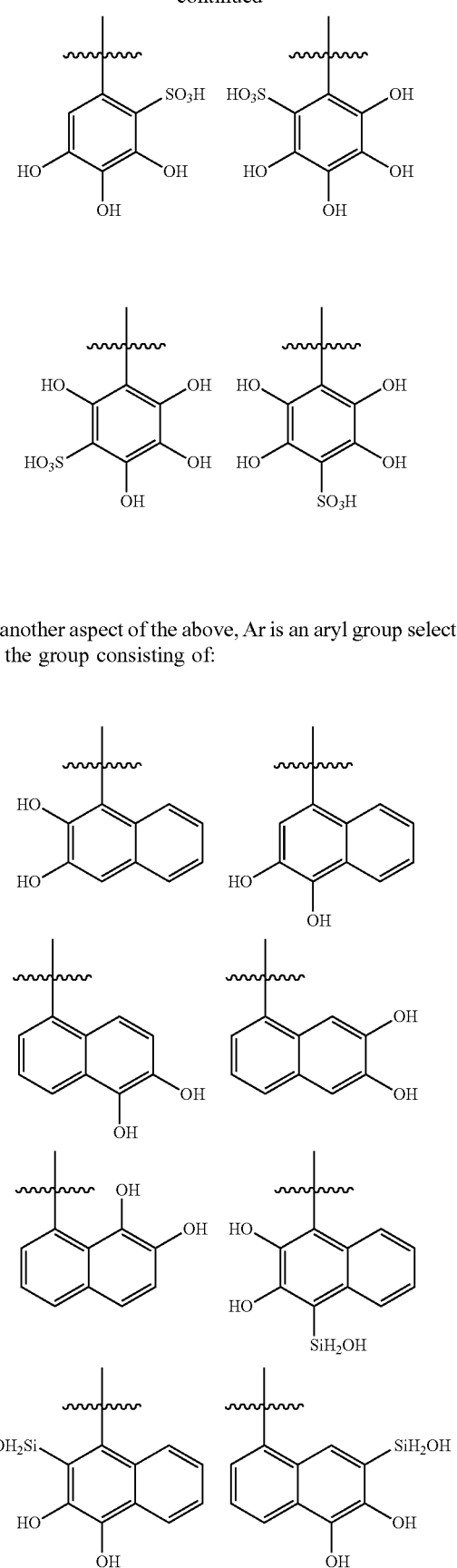

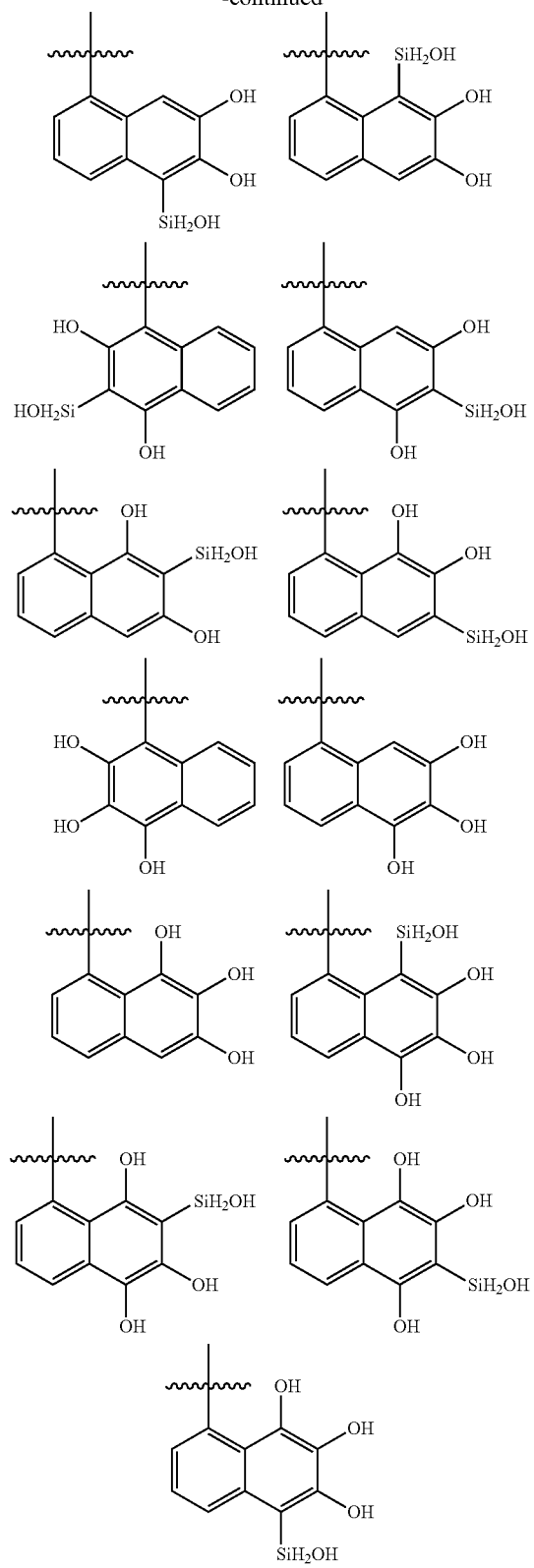
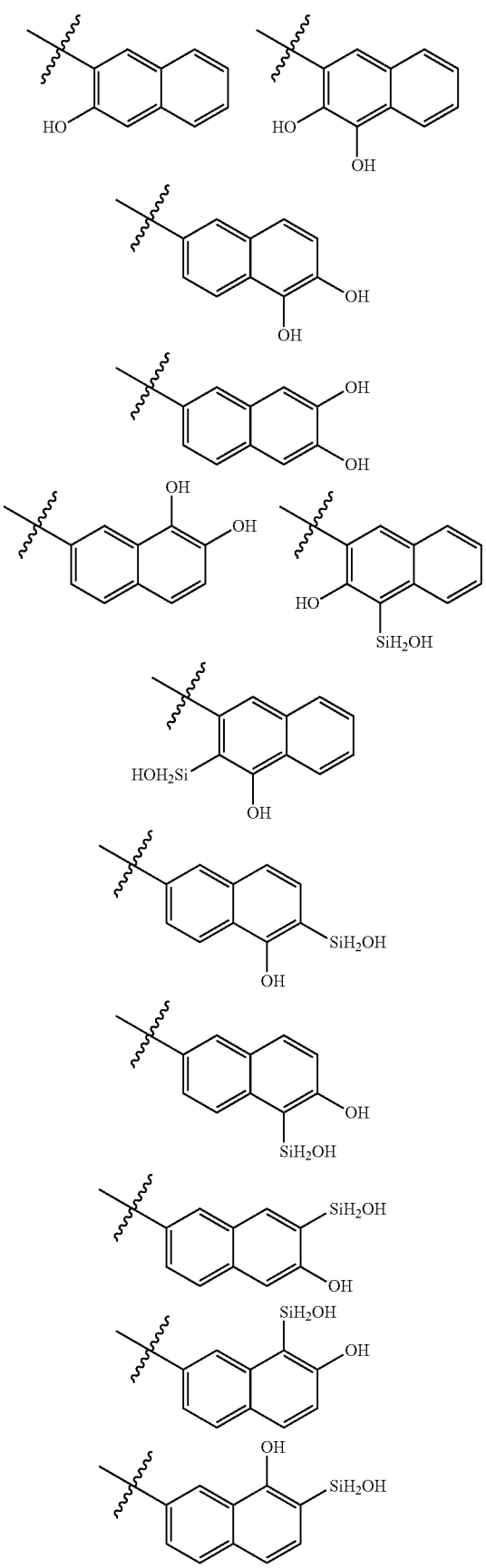
In another aspect of the surface binding compound, Ar is an aryl group selected from the group consisting of:

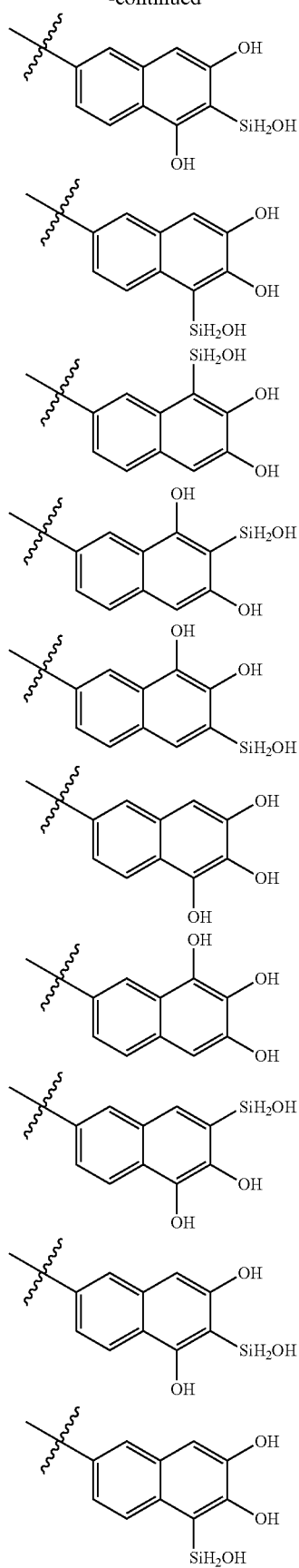
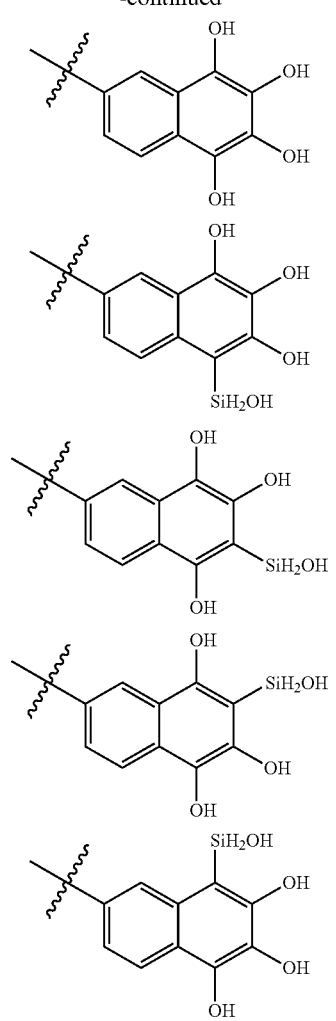
In yet another aspect of the surface binding compound, Ar is an aryl group selected from the group consisting of:
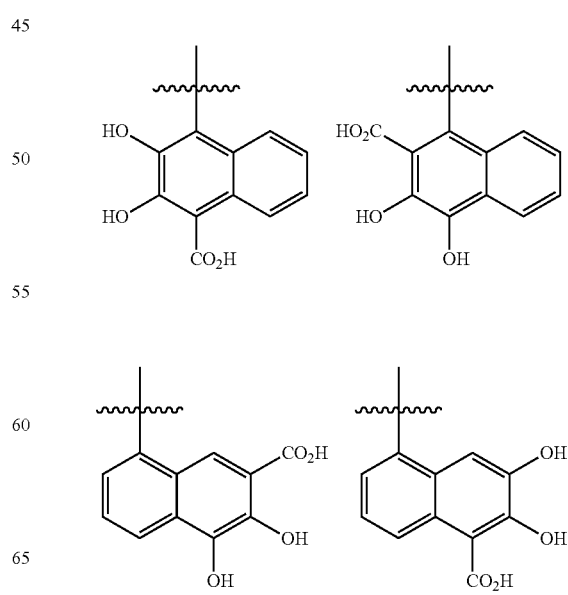

-continued
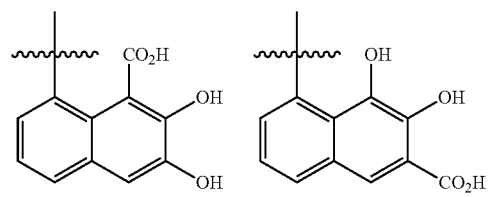
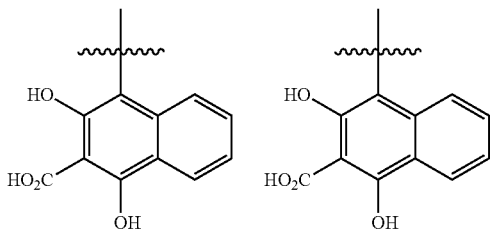
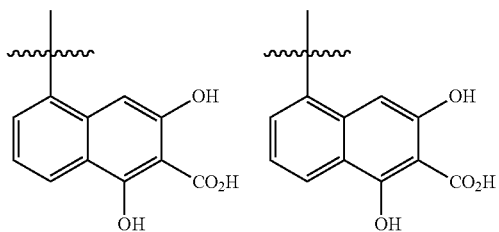
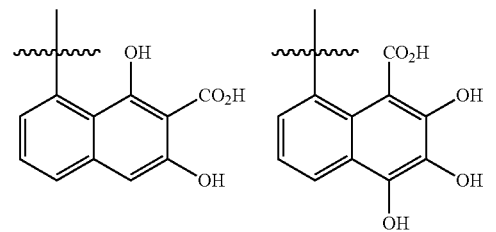
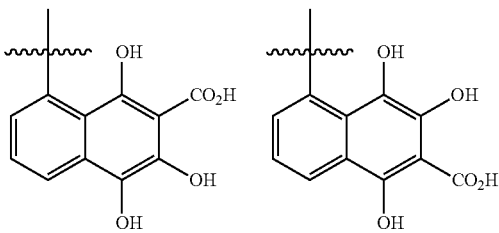
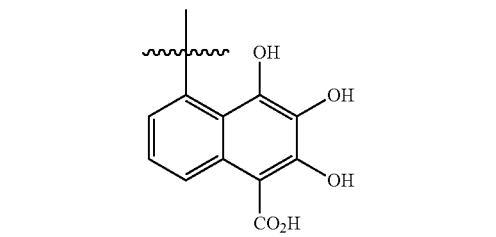
In yet another aspect of the surface binding compound, Ar is an aryl group selected from the group consisting of:
-continued
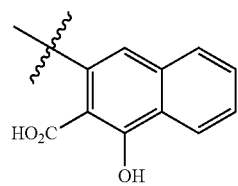
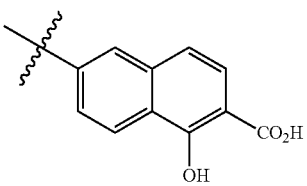
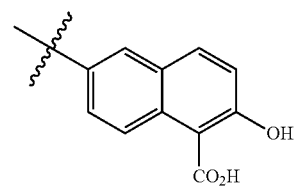
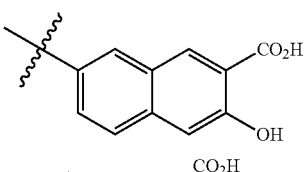
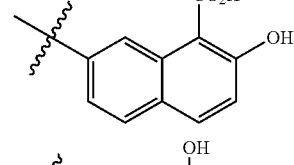
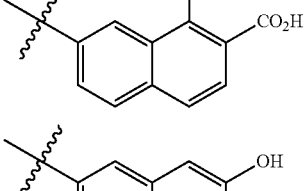
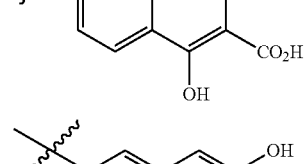
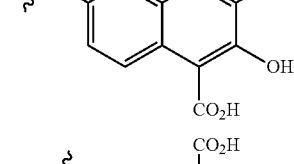
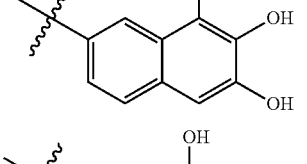
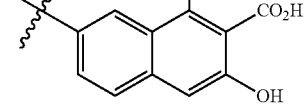

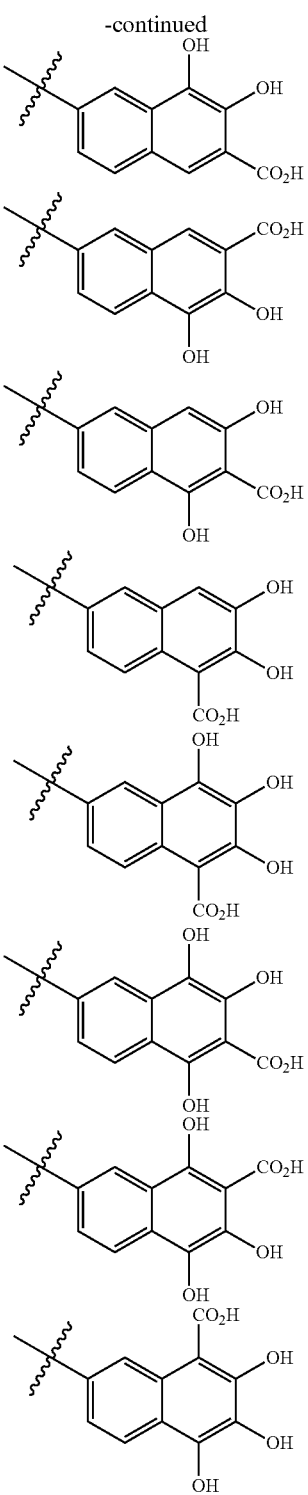

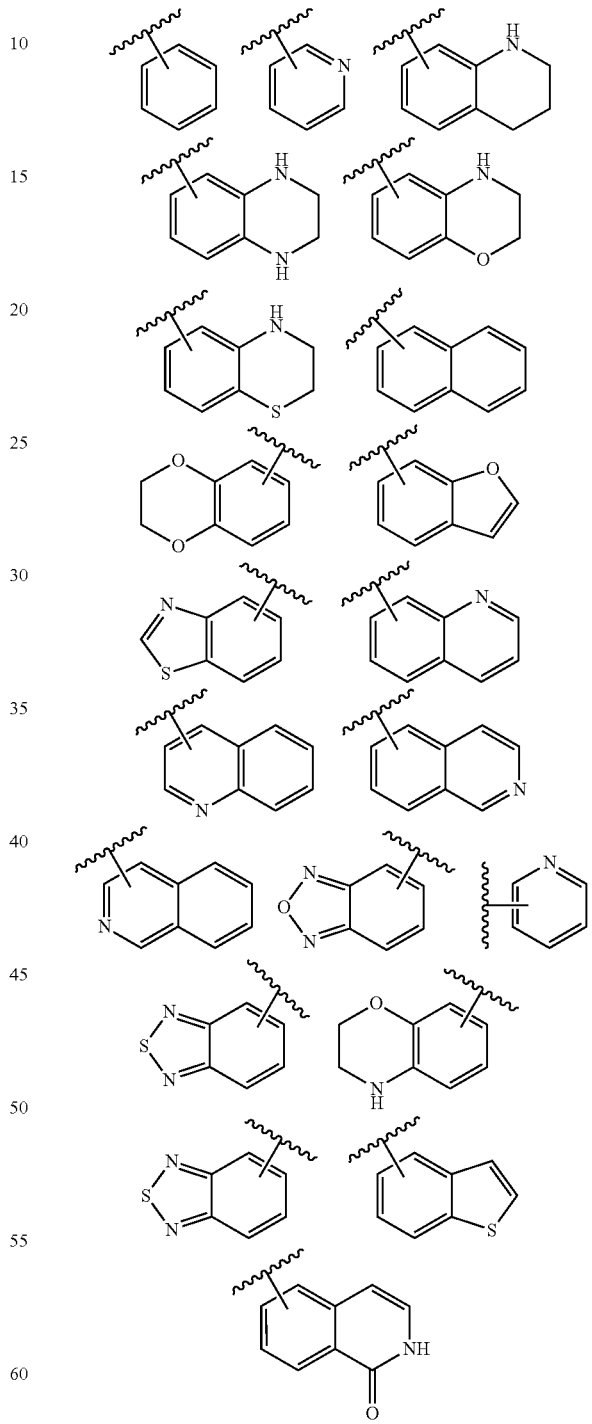

boxyphenyl, 3,4,5-tricarboxylphenyl, 2,3,4,5-tetracarboxyphenyl, 2,3,4,5,6-pentacarboxyphenyl, 2,3-disiloxyphenyl, 2,3,4-trisiloxyphenyl, 3,4,5-trisiloxyphenyl, 2,3,4,5-tetrasiloxyphenyl and 2,3,4,5,6-pentasiloxyphenyl.

In another aspect of the surface binding compound, EG is an aryl group selected from the group consisting of:

wherein the aryl group is optionally substituted by 1 or 2 substituents selected from halo, $CF_3$—, $CF_3O$—, $CH_3O$—, —C(O)OH, —C(O)O$C_{1-3}$alkyl, —C(O)$CH_3$, —CN, —$NH_2$, —OH, —Si(R)$_2$OH, —NHCH$_3$, —N(CH$_3$)$_2$ and In another aspect of the surface binding compound, each BG is a bonding group independently selected from the group consisting of —OH, —Si(R)$_2$OH, —NH$_2$, —NHR, —COOH, —SO$_3$H, —P(O)$_3$OH, —CONH$_2$ and —CSNH$_2$. In another aspect of the surface binding compound, —SP3- is —CH$_2$— and Ar—(BG)$_a$ is selected from the group consisting of 2,3-dihydroxyphenyl, 2,3,4-trihydroxyphenyl, 3,4,5-trihydroxyphenyl, 2,3,4,5-tetrahydroxyphenyl, 2,3,4,5,6-pentahydroxyphenyl, 2,3-dicarboxyphenyl, 2,3,4-tricar- $C_{1-3}$alkyl. In one variation, EG is a cationic, anionic, zwitterionic, polar and non-polar group. In another variation, m is 2 or 3, and the acrylate is a di-acrylate or a tri-acrylate. In one variation, m is 1 and n is 1. In one variation, p is 1, 2, 3, 4, 5 or 6, q is 1, 2, 3, 4, 5 or 6 and r is 1, 2, 3, 4, 5 or 6.

In another aspect, the surface binding compound is selected from the group:

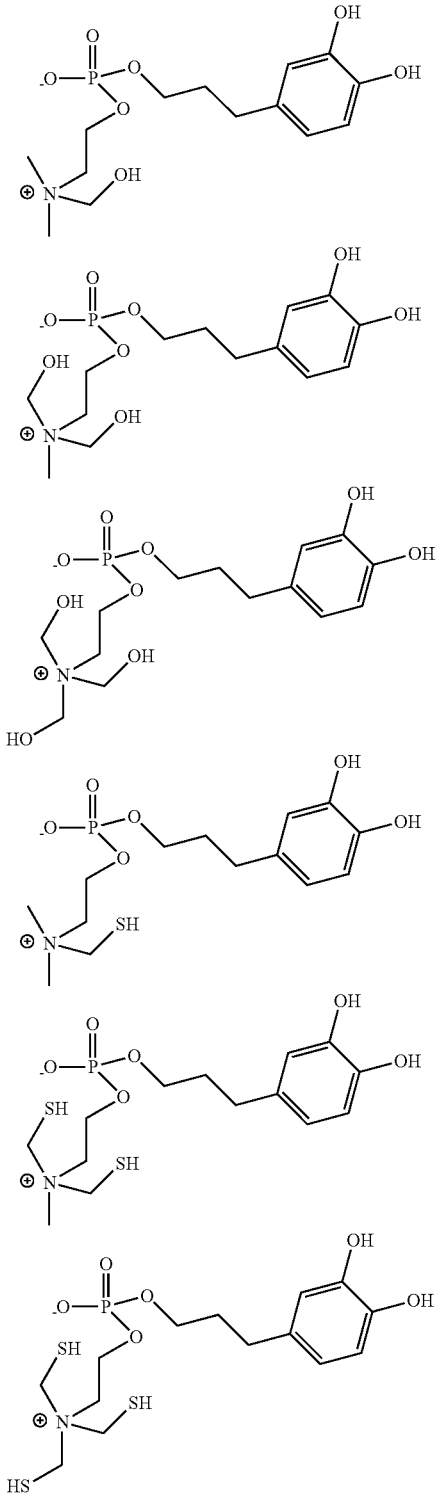

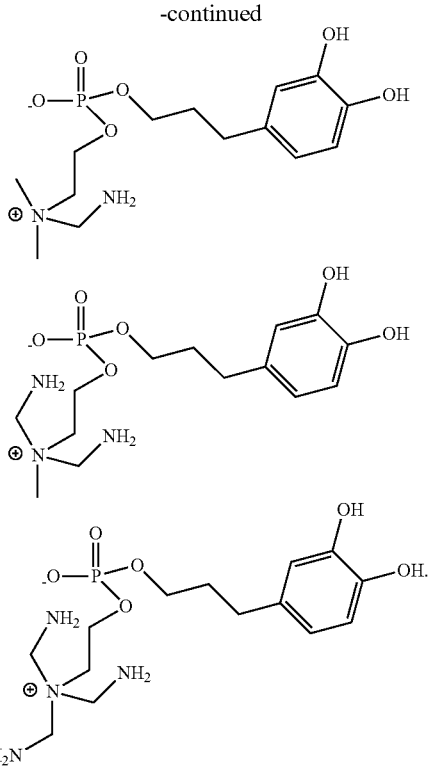

In one particular variation, all of the BG groups on Ar are all adjacent to one another, such as being 1,2,3-substituted on a ring, such as a phenyl or naphthyl ring. In one embodiment, each BG is —OH. In one variation, BG is —OH, —COOH and —OH. In another variation, BG is —OH, —Si(R)$_2$OH or —OH, or a combination thereof. In one variation, R is H or —CH$_3$. In another variation of the compound of the Formula I, the molecular weight of Formula I is less than 2 kDa, less than 1 kDa or less than 0.5 kDa.

In another embodiment, there is provided a method for forming a coating on a surface of a substrate, the method comprises:
1) washing the surface of the substrate with a first solvent;
2) contacting the surface binding compound of the Formula I, optionally in a second solvent, to the surface:

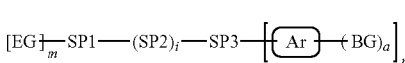

wherein:
each a is independently 1, 2, 3, 4 or 5;
m is 1, 2 or 3; n is 1, 2 or 3; i is 1, 2 or 3;
each EG is an end group independently selected from the group consisting of a $C_{1-12}$alkyl, $CH_2$=CH—, $CH_2$=C($C_{1-3}$alkyl)-, $CH_2$=CHC(O)—, $CH_2$=C($C_{1-3}$alkyl)C(O)—, $CH_2$=CHC(O)O—, $CH_2$=C($C_{1-3}$alkyl)C(O)O—, $CH_2$=C(phenyl)C(O)O—, $CH_2$=C($C_{1-3}$alkyl)S(O)$_n$O—, isocyanate, epoxy, oxetanyl, styrenyl, vinyl ether, (OH)Si(R)$_2$—, (OH)Si(R)$_2$(O)—, —Ar—(BG)$_a$, aryl, heteroaryl, —N$^+$R$_1$R$_2$R$_3$, —PO$_4^-$, —N$^+$R$_1$R$_2$R$_3$X$^-$, —PO$_4^-$Y$^+$ and —SO$_4^-$Y$^+$, wherein each R, R$_1$, R$_2$ and R$_3$ is independently H and $C_{1-3}$alkyl, or optionally substituted $C_{1-3}$alkyl, or wherein $R_1$, $R_2$ and $R_3$ are combined with N to form a heterocyclic compound, $X^-$ is $Cl^-$, $Br^-$ and $I^-$ and $Y^+$ is $H^+$ or $N^+R_1R_2R_3$;

each of SP1, SP2 and SP3 is a spacer independently selected from the group consisting of —O—, —C(O)—, —S—, —S(O)—, —S(O)$_2$—, —N—, —NH—, —NCH$_3$—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —NH(CH$_2$)$_2$NH—, —OC(O)—, —CO$_2$—, —NHCH$_2$CH$_2$C(O)—, —OCH$_2$CH$_2$C(O)—, —C(O)CH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$—, —(CH$_2$)$_q$—N$^+$R$_1$R$_2$—, —(CH$_2$)$_q$PO$_4^-$, —N$^+$R$_1$R$_2$—, —PO$_4^-$—, —(CH$_2$)$_q$—N$^+$R$_1$R$_2$—X$^-$—, —(CH$_2$)$_q$—PO$_4^-$Y$^+$—, —N$^+$R$_1$R$_2$—X$^-$—, —PO$_4^-$Y$^+$—, —SO$_4^-$Y$^+$—, —O—PO$^-$(O)O—(CH$_2$)$_{2-4}$—N$^+$(R$_1$R$_2$)—, -(AA)$_r$-, aryl, cyclopentanyl, cyclohexanyl, unsubstituted phenylenyl and phenylenyl substituted by 1 or 2 substituents selected from the group consisting of halo, CF$_3$—, CF$_3$O—, CH$_3$O—, —C(O)OH, —C(O)OC$_{1-3}$alkyl, —C(O)CH$_3$, —CN, —NH$_2$, —OH, —NHCH$_3$, —N(CH$_3$)$_2$ and C$_{1-3}$alkyl, wherein each AA is independently an amino acid, p is 1-6, q is 1-6 and r is 1-6;

Ar is an aryl group;

each BG is a bonding group independently selected from the group consisting of —OH, —Si(R)$_2$OH, —COOH, —SO$_3$H, —P(O)$_3$OH, —CONH$_2$, —CSNH$_2$, —CF$_3$, —CF$_2$CF$_3$, —OCF$_3$ and —OCF$_2$CF$_3$; provided that when —SP$^3$— is —CH$_2$— or —C(O)—, Ar—(BG)$_a$ is not 3,4-dihydroxyphenyl or 3,4-dicarboxyphenyl;

3) for a period of time for the compound of the Formula I to form a layer on the surface of the substrate; and optionally 4) washing the excess compound of the Formula I from the surface of the substrate with a sufficient amount of a third solvent to remove excess compound from the surface.

A method for forming a coating on a surface of a substrate, the method comprises:

1) washing the surface of the substrate with a first solvent;

2) contacting the surface binding compound of the Formula II, optionally in a second solvent, to the surface:

$$[EG]_m\text{—SP1—(SP2)}_i\text{—SP3—}[EG1]_n \qquad \text{II}$$

wherein: m is 1, 2 or 3; n is 1, 2 or 3; i is 1, 2 or 3;

each EG and EG1 is an end group independently selected from the group consisting of a C$_{1-12}$alkyl, CH$_2$=CH—, CH$_2$=C(C$_{1-3}$alkyl)-, CH$_2$=CHC(O)—, CH$_2$=C(C$_{1-3}$alkyl)C(O)—, CH$_2$=CHC(O)O—, CH$_2$=C(C$_{1-3}$alkyl)C(O)O—, CH$_2$=C(phenyl)C(O)O—, CH$_2$=C(C$_{1-3}$alkyl)S(O)$_n$O—, isocyanate, epoxy, oxetanyl, styrenyl, vinyl ether, (OH)Si(R)$_2$—, (OH)Si(R)$_2$(O)—, —Ar—(BG)$_a$, aryl, heteroaryl, —N$^+$R$_1$R$_2$R$_3$, —PO$_4^-$, —N$^+$R$_1$R$_2$R$_3$X$^-$, —PO$_4^-$Y$^+$, —SO$_4^-$Y$^+$, wherein each R, R$_1$, R$_2$ and R$_3$ is independently H and C$_{1-3}$alkyl or optionally substituted C$_{1-3}$alkyl, or wherein R$_1$, R$_2$ and R$_3$ are combined with N to form a heterocyclic compound, X$^-$ is Cl$^-$, Br$^-$ and I$^-$ and Y$^+$ is H$^+$ or N$^+$R$_1$R$_2$R$_3$;

each of SP1, SP2 and SP3 is a spacer independently selected from the group consisting of —O—, —C(O)—, —S—, —S(O)—, —S(O)$_2$—, —N—, —NH—, —NCH$_3$—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —NH(CH$_2$)$_2$NH—, —OC(O)—, —CO$_2$—, —NHCH$_2$CH$_2$C(O)—, —OCH$_2$CH$_2$C(O)—, —C(O)CH$_2$CH$_2$C(O)—, —C(O)NHCH$_2$CH$_2$NH—, —NHCH$_2$C(O)—, —NHC(O)—, —C(O)N—, —NC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$—, —(CH$_2$)$_q$—N$^+$R$_1$R$_2$—, —(CH$_2$)$_q$PO$_4^-$, —N$^+$R$_1$R$_2$—, —PO$_4^-$—, —(CH$_2$)$_q$—N$^+$R$_1$R$_2$—X$^-$—, —(CH$_2$)$_q$—PO$_4^-$Y$^+$—, —N$^+$R$_1$R$_2$—X$^-$—, —PO$_4^-$Y$^+$—, —SO$_4^-$Y$^+$—, —O—PO$^-$(O)O—(CH$_2$)$_{2-4}$—N$^+$(R$_1$R$_2$)—, -(AA)$_r$-, aryl, cyclopentanyl, cyclohexanyl, unsubstituted phenylenyl and phenylenyl substituted by 1 or 2 substituents selected from the group consisting of halo, CF$_3$—, CF$_3$O—, CH$_3$O—, —C(O)OH, —C(O)OC$_{1-3}$alkyl, —C(O)CH$_3$, —CN, —NH$_2$, —OH, —NHCH$_3$, —N(CH$_3$)$_2$ and C$_{1-3}$alkyl, wherein each AA is independently an amino acid, p is 1-6, q is 1-6 and r is 1-6;

3) for a period of time for the compound of the Formula II to form a layer on the surface of the substrate; and optionally, 4) washing the excess compound of the Formula II from the surface of the substrate with a sufficient amount of a third solvent to remove excess compound from the surface.

In one variation of the method, the compound used is a compound of the Formula I, or Formula II, the compound of the Formula I or Formula II and the compounds as disclosed herein; or a mixture of the compound of the Formula I, or Formula II, to provide the desired adhesive, mechanical or electronic properties of the substrate. In another variation, the first solvent is water, an organic solvent or a mixture of water and the organic solvent. In a particular variation, the organic solvent is selected from the group consisting of methanol, ethanol, propanol, isopropanol, acetone, methylethyl ketone, hexane, cyclohexane, heptane, toluene, xylenes, THF, Me-THF and N-methylpyrrolidone, or mixtures thereof. In another variation, the first, second and third solvents are the same or are different, and are selected from the group consisting of water, methanol, ethanol, a mixture of water and methanol, a mixture of water and ethanol or a combination thereof. In another variation, the first solvent is different than the second and the third solvents.

In another aspect of the method, each EG is independently selected from the group consisting of a C$_{1-12}$alkyl, optionally substituted C$_{1-3}$alkyl, —N(CH$_3$)$_2$CH$_2$OH, —N(CH$_2$OH)$_2$CH$_3$, —N(CH$_2$OH)$_3$, —N(CH$_2$CH$_3$)$_2$CH$_2$CH$_2$OH, —N(CH$_2$CH$_2$OH)$_2$CH$_2$CH$_3$, —N(CH$_2$CH$_2$OH)$_3$, —N(CH$_3$)$_2$CH$_2$SH, —N(CH$_2$SH)$_2$CH$_3$, —N(CH$_2$SH)$_3$, —N(CH$_2$CH$_3$)$_2$CH$_2$CH$_2$SH, —N(CH$_2$CH$_2$SH)$_2$CH$_2$CH$_3$, —N(CH$_2$CH$_2$SH)$_3$, —N(CH$_3$)$_2$CH$_2$NH$_2$, —N(CH$_2$NH$_2$)$_2$CH$_3$, —N(CH$_2$NH$_2$)$_3$, —N(CH$_2$CH$_3$)$_2$CH$_2$CH$_2$NH$_2$, —N(CH$_2$CH$_2$NH$_2$)$_2$CH$_2$CH$_3$, —N(CH$_2$CH$_2$NH$_2$)$_3$, —N$^+$(CH$_3$)$_2$CH$_2$OH X$^-$, —N$^+$(CH$_2$OH)$_2$CH$_3$X$^-$, —N$^+$(CH$_2$OH)$_3$X$^-$, —N$^+$(CH$_2$CH$_3$)$_2$CH$_2$CH$_2$OH X$^-$, —N$^+$(CH$_2$CH$_2$OH)$_2$CH$_2$CH$_3$X$^-$, —N$^+$(CH$_2$CH$_2$OH)$_3$X$^-$, —N$^+$(CH$_3$)$_2$CH$_2$SH X$^-$, —N$^+$(CH$_2$SH)$_2$CH$_3$X$^-$, —N$^+$(CH$_2$SH)$_3$X$^-$, —N$^+$(CH$_2$CH$_3$)$_2$CH$_2$CH$_2$SH X$^-$, —N$^+$(CH$_2$CH$_2$SH)$_2$CH$_2$CH$_3$X$^-$—N$^+$(CH$_2$CH$_2$SH)$_3$X$^-$, —N$^+$(CH$_3$)$_2$CH$_2$NH$_2$X$^-$, —N$^+$(CH$_2$NH$_2$)$_2$CH$_3$X$^-$, —N$^+$(CH$_2$NH$_2$)$_3$X$^-$, —N$^+$(CH$_2$CH$_3$)$_2$CH$_2$CH$_2$NH$_2$X$^-$, —N$^+$(CH$_2$CH$_2$NH$_2$)$_2$CH$_2$CH$_3$X$^-$—N$^+$(CH$_2$CH$_2$NH$_2$)$_3$X$^-$CH$_2$=CHC(O)O—, CH$_2$=C(C$_{1-3}$alkyl)C(O)O—, CH$_2$=C(phenyl)C(O)O—, CH$_2$=CHS(O)$_n$O—, isocyanate, epoxy, oxetanyl, styrenyl, vinyl ether, —Ar—(BG)$_a$, phenyl and naphthyl, where X$^-$ is Cl$^-$, Br$^-$ and I$^-$. In another aspect of the method, each EG is independently selected from the group consisting of an aryl, heteroaryl, imidazolyl, imidazolinium, indolinium, indolyl, —N⁺R₁R₂R₃, —PO₄⁻, —N⁺R₁R₂R₃X⁻, —PO₄⁻Y⁺, —SO₄⁻Y⁺, wherein each R₁, R₂ and R₃ is independently H and C₁₋₃alkyl and C₁₋₃alkyl substituted with 1, 2 or 3 —OH or 1, 2 or 3 —NH₂, X⁻ is Cl⁻, Br⁻ and I⁻ and Y⁺ is H⁺ or —N⁺R₁R₂R₃. In one variation, R, R₁, R₂ and R₃ is independently C₁₋₃alkyl optionally substituted with —OH, —SH or —NH₂.

In another aspect of the method, each of SP1, SP2 and SP3 is a spacer independently selected from the group consisting of —(CH₂)_q—, —NH(CH₂)₂NH—, —NHCH₂CH₂C(O)—, —C(O)NHCH₂CH₂NH—, —NHCH₂C(O)—, —NHC(O)—, —C(O)N—, —NC(O)—, —C(O)NH—, —NCH₃C(O)—, —C(O)NCH₃—, —(CH₂CH₂O)_p—, —(CH₂CH₂O)_pCH₂CH₂—, —CH₂CH₂—(CH₂CH₂O)_p— and —OCH(CH₂O—)₂-. In another aspect, each of SP1, SP2 and SP3 is a spacer independently selected from the group consisting of —N⁺R₁R₂—, —PO₄⁻—, —N⁺R₁R₂X⁻—, —PO₄⁻Y⁺—, —SO₄⁻Y⁺—, —(CH₂)_q—N⁺R₁R₂—, —(CH₂)_q—PO₄⁻—, —(CH₂)_q—N⁺R₁R₂—X⁻—, —(CH₂)_q—PO₄⁻Y⁺— and —O—PO—(O)O—(CH₂)₂₋₄—N⁺(R₁R₂)—. In yet another aspect of the method, SP1, SP2 and SP3 is independently selected from the group consisting of —CH₂CH₂—C(O)NHCH₂CH₂NH—C(O)NCH₃—, —NHC(O)—(CH₂CH₂O)_p—(CH₂)_q—, —(CH₂CH₂O)_pCH₂CH₂—C(O)NCH₃—(CH₂CH₂O)_pCH₂CH₂—, —NHCH₂CH₂C(O)—(CH₂)_q—PO₄⁻—, —PO₄⁻—(CH₂)_q—N⁺R₁R₂X⁻—, —(CH₂CH₂O)_p—(CH₂)_q—PO₄⁻, —N⁺R₁R₂X⁻—(CH₂)_q—PO₄⁻ and —PO₄⁻—(CH₂CH₂O)_p—N⁺R₁R₂X⁻—.

In another aspect of the method, Ar is an aryl group selected from the group consisting of:

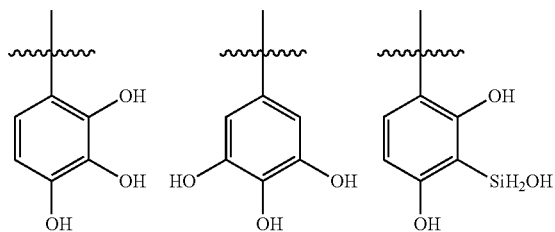

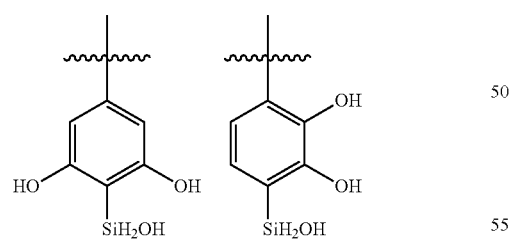

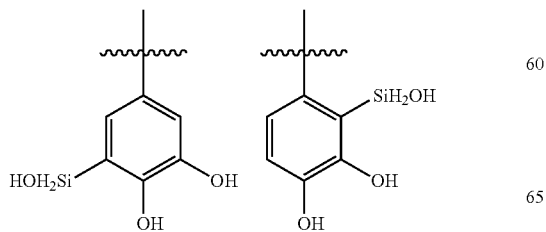

-continued

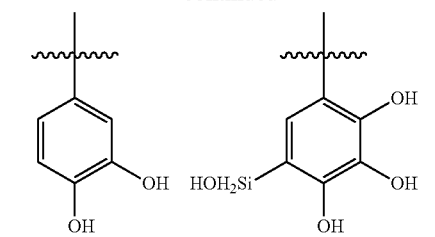

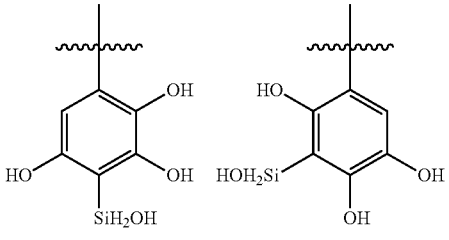

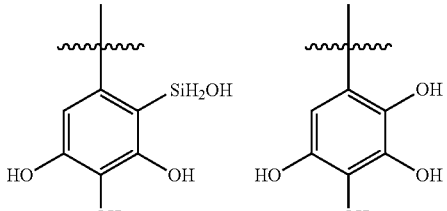

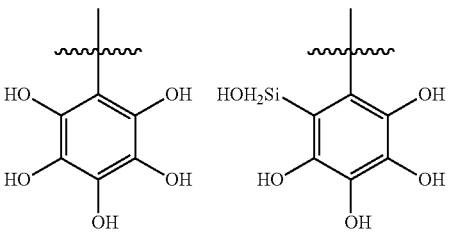

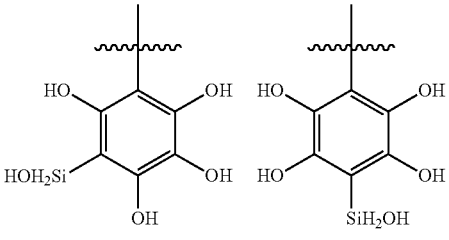

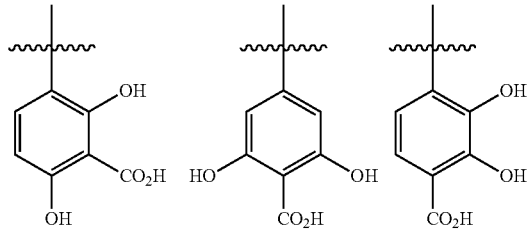

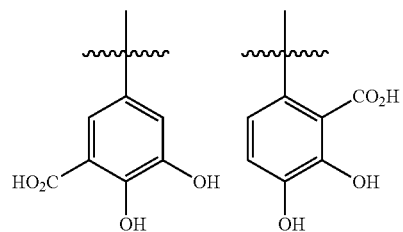

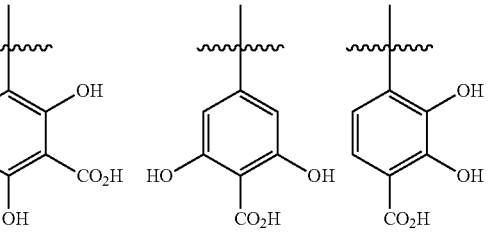

-continued

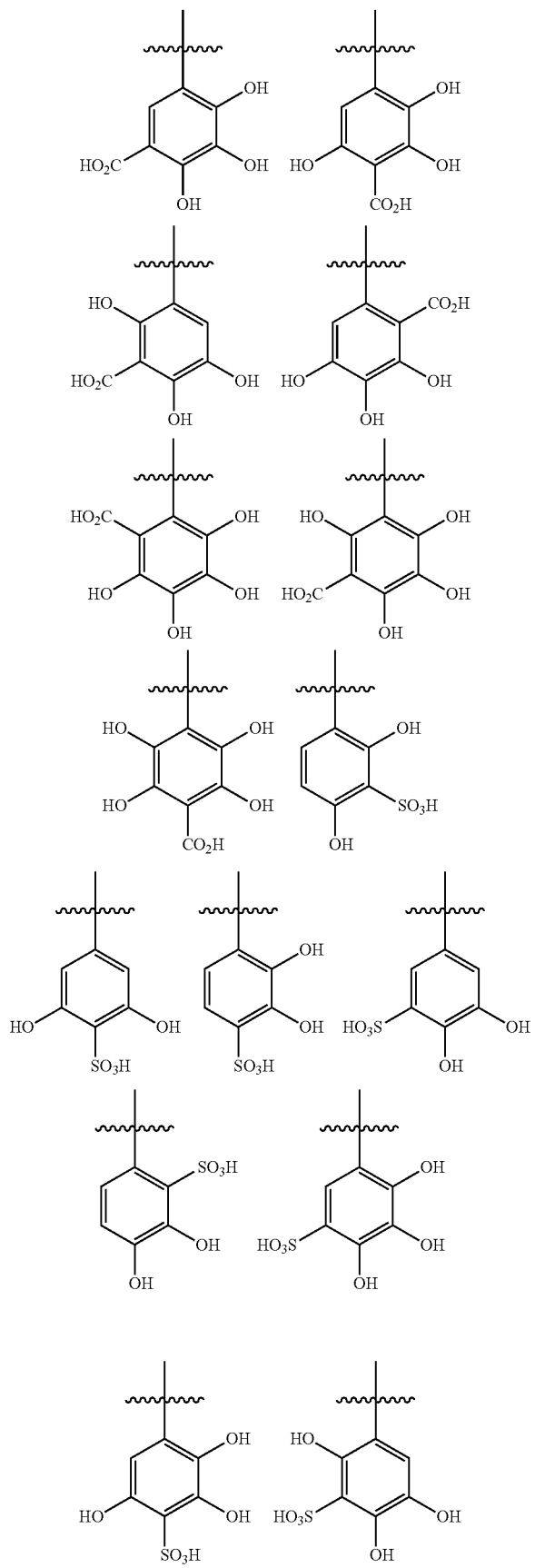

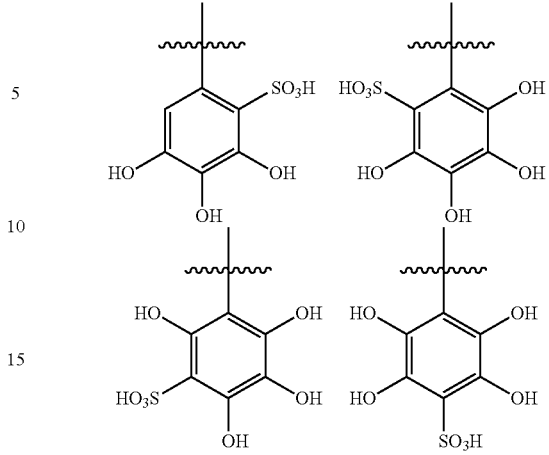

In another aspect of the method, each BG is a bonding group independently selected from the group consisting of —OH, —Si(R)$_2$OH, —COOH, —SO$_3$H, —P(O)$_3$OH, —CONH$_2$ and —CSNH$_2$. In yet another aspect, —SP3- is —CH$_2$— and Ar-(BG)$_a$ is selected from the group consisting of 2,3-dihydroxyphenyl, 2,3,4-trihydroxyphenyl, 3,4,5-trihydroxyphenyl, 2,3,4,5-tetrahydroxyphenyl, 2,3,4,5,6-pentahydroxyphenyl, 2,3-dicarboxyphenyl, 2,3,4-tricarboxyphenyl, 3,4,5-tricarboxylphenyl, 2,3,4,5-tetracarboxyphenyl, 2,3,4,5,6-pentacarboxyphenyl, 2,3-disiloxyphenyl, 2,3,4-trisiloxyphenyl, 3,4,5-trisiloxyphenyl, 2,3,4,5-tetrasiloxyphenyl and 2,3,4,5,6-pentasiloxyphenyl. In one variation, R is H or —CH$_3$.

In another aspect of the method, the coating is formed by a self-assembly of the compound of the Formula I, or Formula II, onto the surface. In yet another aspect of the method, the self-assembled layer is about 0.1 nm to 20 nm, about 0.1 to 15 nm, 0.1 to 10 nm or about 0.1 to 5 nm. In one variation, the self-assembled layer is a self-assembled monolayer (SAM). In one variation, the self-assembled layer forms at less than 40° C., less than 30° C. or at about RT. In another variation, the self-assembled monolayer forms in less than about 60 min, less than 45 min, less than 30 min or less than about 15 min.

In another aspect of the method, the coating is a material selected from an adhesive or a primer. In yet another aspect of the above method, the substrate is selected from the group consisting of an oxide, a metal, a metal oxide and a mineral. In another aspect, the substrate is selected from the group consisting of mica, silicon, glass, calcium, enamel, bone, steel, tooth enamel, tooth dentin, hydroxylapatite, kaolin and zirconia. In another aspect, the metal, metal oxide or oxide is selected from the group consisting of silicate mineral, silica, kaolin, zirconia, aluminum, copper, chrome, chrome-cobalt, titanium, zinc, tin, indium-tin and calcium oxide.

In another aspect of the method, the adhesive is formed by contacting the tail end of the self-assembled layer comprising the -EG groups of the substrate that is the first substrate, with the tail end of a second substrate comprising a surface binding compound of the Formula I, whereby the tail end of the compound of the Formula I of the first substrate binds with the tail end of the compound of the Formula I of the second substrate. In one variation, the compound of the Formula I in the first substrate is the same or different than the compound of the Formula I in the second substrate. In another variation, the head end of the compound of the Formula I binds with the surface of the substrate via hydrogen bonds, chelation, metal-oxygen coordination bond or via a covalent bond.

In another aspect of the method, the adhesive is formed by contacting the tail end of the self-assembled layer comprising the -EG groups of the substrate that is the first substrate, with the tail end of a second substrate comprising a surface binding compound of the Formula II, whereby the tail end of the compound of the Formula II of the first substrate binds with the tail end of the compound of the Formula II of the second substrate. In one variation, the compound of the Formula II in the first substrate is the same or different than the compound of the Formula II in the second substrate. In another variation, the head end of the compound of the Formula II binds with the surface of the substrate via hydrogen bonds, chelation, metal-oxygen coordination bond or via a covalent bond.

In another aspect of the method, the adhesive forms an adhesive layer for dental application, medical implants and orthopedic applications. In one variation, the adhesive layer may be used as an enamel adhesive or cement or a bone adhesive or cement. For dental applications, the adhesive layer may be used as a filling, a general adhesive, a cavity liner, a dental cement, a coating composition with or without filler, a root canal filler or sealant with or without filler or a combination thereof. In one variation the adhesive layer may be a self-adhesive composition or a photo-curable composition.

In another aspect of the method, the metal oxide is selected from the group consisting of aluminum oxide, copper oxide, chrome, chrome-cobalt, titanium oxide, zinc oxide, tin oxide and indium-tin-oxide (ITO). In yet another aspect of the method, the substrate is selected from the group consisting of polytetrafluorethylene (PTFE), silicon, silicon wafer, polyvinyl fluoride (PVF), natural rubber (CR), polypropylene (PP), polyethylene (PE), polymethyl methacrylate, acryl (PMMA), epoxy (EP), polyoxymethylene, acetal (POM), polystyrene (PS), polyvinyl chloride (PVC), vinylidene chloride (VC), polyester (PET), polyimide (PI), polyarylsulfone (PAS), phenolic resin, polyurethane (PUR), polyamide 6 (PA 6), polycarbonate (PC), lead (Pb), aluminum (Al), copper (Cu), chromium (Cr), iron (Fe) and stainless steel (SS).

Methods of forming a SAM coating on a surface of a substrate are known in the art. The SAM or SAM coating that forms the EG group or the —Ar-BG group may include organosilanes or other silane molecules. In one variation, the SAM coating is a chlorosilane, such as a trichlorosilane or a methoxysilane. Trichlorosilanes of a SAM as provided herein may be selected from an n-decyltrichlorosilane (DTS), an n-dodecyltrichlorosilane, a perfluorodecyltrichlorosilane (FDTS) or a n-octadecyltrichlorosilane. As provided herein, a SAM may include dimethylaminosilanes and alklysilanes, and alkyltrichlorosilanes or alkyltrimethoxysilanes. In one variation, the SAM comprises siloxanes such as hexamethyldisilazane (HMDS).

In one variation, the coating is a self-assembled layer or a self-assembled monolayer (SAM) of the compound. In another variation, the surface is a gate dielectric surface for electronic devices, such as an organic field-effect transistor. In another variation, the self-assembled monolayer is ordered and defect-free. In one aspect of the SAMs of the present application, at least 30%, 40%, 50%, 60%, 70%, 80%, 90% or more than 95% of the compounds that adsorb to the surface bond to the surface of the substrate. In another variation, the high bonding layer provides well-defined, uniform and reproducible layers, such as monolayers, that are bonded to the surface of the substrate. The substantially ordered and defect-free layers may be characterized and confirmed using Atomic Force Microscope (AFM), Surface force Apparatus (SFA), X-Ray Scattering and Molecular dynamic (MD) simulation or a combination thereof, as known in the art.

In another variation of the method, the self-assembled layer is a surface modifier used for anode binders, electro circuits, field effect transistors (FET; with range value of 20-50 $cm^2V^{-1}s^{-1}$), semiconductors, nanosensing devices, organic solar cells, opto-electronic devices, hetero junctions and electron tunneling junctions. In one variation of the above, the self-assembled layer is a self-assembled monolayer (SAM).

In another variation, the compound forms a SAM in less than about 60 minutes, less than 30 minutes, less than 10 minutes, less than 5 minutes, less than about 2 minutes or less than about 1 minute, after contacting with the surface of the substrate. In one variation of the method, the compound forms a substantially smooth, uniform and defect-free SAM.

In one variation of the method, the SAM is a surface modifier that produces low contact angles Θ of less than 20°, less than 15°, than 13° or less than 11° for a chlorobenzene droplet. In another variation, the SAM surface modifiers are omniphilic with <30° contact angle for a water droplet. In one variation, the SAM forms a monolayer of about 0.1 nm to 50 nm, 0.1 nm to 40 nm, 0.1 nm to 30 nm, 0.1 nm to 20 nm or about 0.1 nm to 10 nm. In another variation, the SAM forms a monolayer of less than about 5 nm, less than 4 nm, less than 3 nm or less than 2 nm.

In another variation of the method, the method further comprises of providing a layer of organic semiconducting material over the layer of the self-assembled layer or SAM. In accordance with one variation of the above described methods, the method provides an improved organic thin-film transistor or other similar electronic devices. In one aspect of the method, the self-assembled layer may comprise a self-assembled monolayer. The self-assembled layer may comprise a polymer layer. In one variation of the method, the self-assembled layer may have a surface region that is hydrophobic and/or oleophillic.

In one variation of the above adhesive, the bonding strength or the shear fracture strength is at least 15 kT, greater than 20 kT, greater than 25 kT, greater than 30 kT, greater than 35 kT, greater than 40 kT, greater than 45 kT or greater than 50 kT. In one variation of the method, the adhesion is at least 30 mJ $m^{-2}$, 35 mJ $m^{-2}$, 40 mJ $m^{-2}$ or at least 45 mJ $m^{-2}$.

In some embodiments, the compound of Formula I may be used as a primer or a coating. As disclosed herein, the compound of Formula I provides strong adhesion/adsorption and retains the ability to interact or bond with a secondary layer. The compound may adhere to a variety of surfaces and undergo self-assembly to form a thin primer/coating/glue/adhesive layer. In some embodiments, the primer/coating/glue/adhesive layer has a thickness from between 0.5 to 50 nm.

In some embodiments as disclosed herein, the compound of Formula I can be applied onto mineral or metal oxide surfaces, such as mica, silicon wafer, glass, bone, tooth enamel, tooth dentin, medical/dental implant, silica, kaolin, zirconia, aluminum, copper, chrome, chrome-cobalt, calcium, aluminum oxide, copper oxide, silica oxide, titanium oxide, zinc oxide, calcium oxide, tin oxide, indium-tin oxide or hydroxylapatite.

In some embodiments, the deposited layer of the compound of Formula I may be treated with an oxidizing agent, such as periodate. In other embodiments, the layer may be treated with a base. Based on the hydroxyl-phenyl groups that are similar to the molecule dopa, at low pH, the hydroxyl phenyl groups are structurally favored over the corresponding keto or quinone-like structures, which provide higher bonding forces. Accordingly, the reverse relative bonding forces are provided at higher pH. Under substantially neutral pH conditions, a strong adhesive of the compound to the substrate may be associated with the interaction of the surfaces with the unoxidized hydroxyl phenyl groups, and the weaker adhesive interaction of the compounds with the surface may be associated with the corresponding oxidized hydroxyl phenyl groups to the oxo- or quinone-type functionality. The surface bound materials may be treated with an oxidizing agent, or may be treated with a base to adjust or modify the binding strength of the coating to the substrate.

In some embodiments, the deposited layers of the present application comprises a mixture of anionic and cationic groups, such as an anionic or cationic terminal groups, provide anti-adsorption properties toward certain compositions, such as proteins, and provide effective anti-fouling surfaces. As disclosed herein, the compounds comprise, for example, a phosphate group and an ammonium salt, that form zwitterionic groups that are highly effective as anti-fouling compositions and surfaces. In addition, the coating has the ability to resist the adsorption of bacteria, barnacle cypris larvae and algal zoospores, and accordingly prevent marine fouling of the surfaces. In addition, the surface materials are also effective as antibacterial surfaces for different medical applications.

As disclosed herein, the anionic and cationic functional groups may be incorporated at an internal position in the compound of the Formula I, incorporated at an internal position and at the terminal position, and various combinations thereof. According to one embodiment, the surface coating provides highly effective anti-fouling surfaces or prevents biofoulants from attaching to the surfaces, and accordingly, provides an effective grafting method that provides substrates with better mechanical and chemical robustness and significantly better long term stability.

In some embodiments, the compounds of Formula I may be used as dental/bone adhesives, surface primers for dental/medical implants, surface primers for mineral fillers used for polymer composites including dental and bone cements/adhesives/composites or electronic devices.

In one embodiment, the compounds disclosed may be formulated with conventional primers. For example, catechol-SP-acrylates (or methacrylates) may be mixed with a phospho-SP-acrylates (or methacrylates) or silane-SP-acrylate (or methacrylates); or mixtures thereof.

In addition to the exemplary embodiments, aspects and variations described above, further embodiments, aspects and variations will become apparent by reference to the drawings and figures and by examination of the following descriptions.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustrated in the figures, and it is intended that the embodiments, aspects and variations, and the figures disclosed herein are to be considered illustrative and not limiting. The entire disclosures of all documents cited throughout this application are incorporated herein by reference.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $(C_{1-20})$alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a $-(CR^1R^2)_m-$ group where $R^1$ and $R^2$ are independently hydrogen or are independently absent, and for example, m is 1 to 8, and such representation is also intended to cover both saturated and unsaturated alkyl groups.

An alkyl as noted with another group such as an aryl group, represented as "arylalkyl" for example, is intended to be a straight, branched, saturated or unsaturated aliphatic divalent group with the number of atoms indicated in the alkyl group (as in $(C_{1-12})$alkyl, for example) and/or aryl group (as in $(C_{5-14})$aryl, for example) or when no atoms are indicated means a bond between the aryl and the alkyl group. Nonexclusive examples of such group include benzyl, phenethyl and the like.

An "alkylene" group is a straight, branched, saturated or unsaturated aliphatic divalent group with the number of atoms indicated in the alkyl group; for example, a $-(C_{1-3})$alkylene- or $-(C_{1-3})$alkylenyl-.

"Amino acids" (AA) are well known in the art and are compounds containing an amine group ($-NH_2$) and a carboxylic acid group ($-COOH$), usually functionalized with a side chain for each amino acid. Amino acids include glycine, alanine, valine, leucine, isoleucine, serine, cysteine, selenocysteine, threonine, methionine, proline, phenylalanine, tyrosine, tryptophan, histidine, lysine, arginine, aspartate, glutamate, asparagine and glutamine. The bonding of two or more amino acids may form a peptide, such as a dipeptide, tripeptide etc. . . .

An "aryl" means a monocyclic or polycyclic ring assembly wherein each ring is aromatic, or when fused with one or more rings, forms an aromatic ring assembly. If one or more ring atoms is not carbon (e.g., N, S), the aryl is a heteroaryl. An aryl group may optionally be substituted as noted herein.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

As used herein, a "dental adhesive" means a compound or composition disclosed herein that may be used as a treatment or pre-treatment on a dental unit or structure (such as a tooth) to adhere to a dental element or material (such as an orthodontic appliance (e.g. a bracket) to a dental surface. The dental adhesive may be generally referred to as a composition used to adhere an orthodontic appliance to a dental surface, such as a tooth surface. In certain aspects, the dental surface may be pre-treated by etching or priming or by applying an adhesive to enhance adhesion with the compound and compositions disclosed herein.

A "filler" or "fillers" are particle(s) and/or fibers added to a material (plastics, adhesives, composite materials, concrete, cement) to lower the consumption of a more expensive material, such as a binder, or to improve the mechanical properties of the mixed materials. The filler may be made of various different materials known in the art, including minerals, e.g., silicate minerals (including mica, silica, glass, kaoline, zirconia etc. . . . ) and biominerals (including calcium carbonate, silica, hydroxyapatite in tooth and bone), and metal/metal oxides, such as aluminum/alumina, titanium/titania etc. . . . For dental applications, a filler or a filler matrix may comprise one filler or a mixture of different fillers. The filler should generally be non-reactive. Representative fillers may include fumed silica, non-acid reactive fluoroaluminosilicate glasses fillers, quartz, ground glasses, non-water-soluble fluorides, silica gels, calcium silicate, zirconium silicate, zeolites and molecular sieves.

"Halogen" or "halo" means fluorine, chlorine, bromine or iodine.

A "heterocyclyl" or "heterocycle" is a cycloalkyl wherein one or more of the atoms forming the ring is a heteroatom that is a N, O, or S. Non-exclusive examples of heterocyclyl include piperidyl, 4-morpholyl, 4-piperazinyl, pyrrolidinyl, 1,4-diazaperhydroepinyl, 1,3-dioxanyl, and the like.

A "heteroaryl" means a cyclic aromatic group having five or six ring atoms, wherein at least one ring atom is a heteroatom e.g., N, S, O) and the remaining ring atoms are carbon. Where present, a nitrogen atom can be optionally quaternerized, and sulfur atoms can be optionally oxidized. Heteroaryl groups include, but are not limited to, those derived from pyridazine, pyridine and pyrimidine. A heteroaryl also includes, but is not limited to, bicyclic or tricyclic rings, where the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, indolizine, imidazo[1,2a]pyridine, quinoline, isoquinoline, phthalazine, quinoxaline, naphthyridine, quinolizine, indole, benzoxazole, benzopyrazole and benzothiazole. The bicyclic or tricyclic heteroaryl rings can be attached through either the heteroaryl group itself or the aryl, cycloalkyl, cycloalkenyl or heterocycloalkyl group to which it is fused. The heteroaryl groups of this invention can be substituted or unsubstituted as noted.

As used herein, a "mechanical property" or "mechanical properties" of a material includes the stiffness, hardness, Young's modulus (elastic modulus), toughness, strain at fracture (extensibility or flexibility), yield strength, ultimate strength, etc. . . . of a material as disclosed in the application.

"Self assembled" or "self assembly" as used in "self-assembled monolayer" or SAMs are organic assembly structures that are formed by the adsorption of molecular compounds from a solution (or a gas phase) onto the surface of substrates or solids. Typically, the adsorbates organize spontaneously (sometimes epitaxially) into crystalline or semicrystalline-like structures. The molecule (or ligand) such as the compound of the Formula I, that form SAMs have a chemical functionality that may be referred to as a "headgroup", with a specific affinity for the surface of a substrate. Once the head group of the compound binds to the surface of a substrate, the end group (EG) or tail group forms the surface of the SAM that may further bind with one or more layers, such as a second or subsequent self-assembled layer or SAM.

"Substituted or unsubstituted" or "optionally substituted" means that a group such as, for example, alkyl, aryl, heterocyclyl, ($C_{1-8}$)cycloalkyl, hetrocyclyl($C_{1-8}$)alkyl, aryl($C_{1-8}$)alkyl, heteroaryl, heteroaryl($C_{1-8}$)alkyl, and the like, unless specifically noted otherwise, may be unsubstituted or, may substituted by 1, 2 or 3 substituents selected from the group such as halo, nitro, $F_3C$—, $F_3CO$—, $CH_3O$—, —C(O)OH, —$NH_2$, —OH, —SH, —$NHCH_3$, —$N(CH_3)_2$, —SMe, cyano and the like.

A "substrate" means a material, a base material or composition with a surface for printing and electronics fabrication and devices. Substrates are well known in the art, and may be used interchangeably with "material."

"Surface primer" or "primer" means a thin layer of material, such as the compound of the Formula I that may form a self-assembled layer, such as a SAM, that may be used to improve the adhesion of surfaces, such as metals, metal oxides, oxides and other materials, with a second layer of material, such as a second self-assembled layer or another SAM.

EXPERIMENTAL

The following procedures may be employed for the preparation of the compounds of the present invention. The starting materials and reagents used in preparing these compounds are either available from commercial suppliers such as the Sigma-Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

Preparation of Primers/Compounds:

The compounds may be prepared using conventional organic synthetic methods.

Scheme 1: Preparation of a representative primer

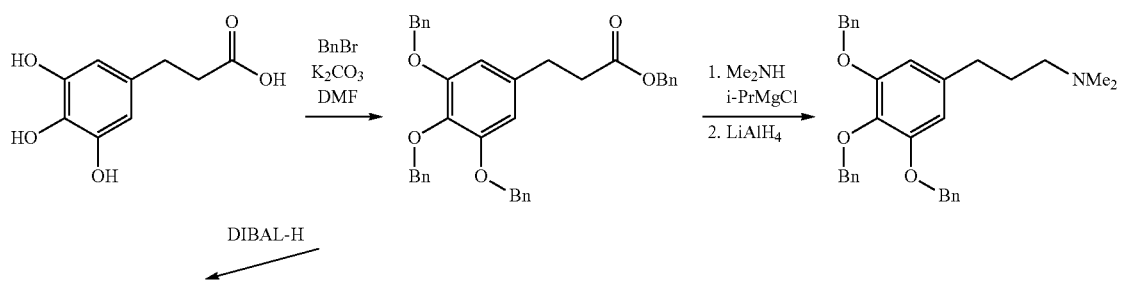

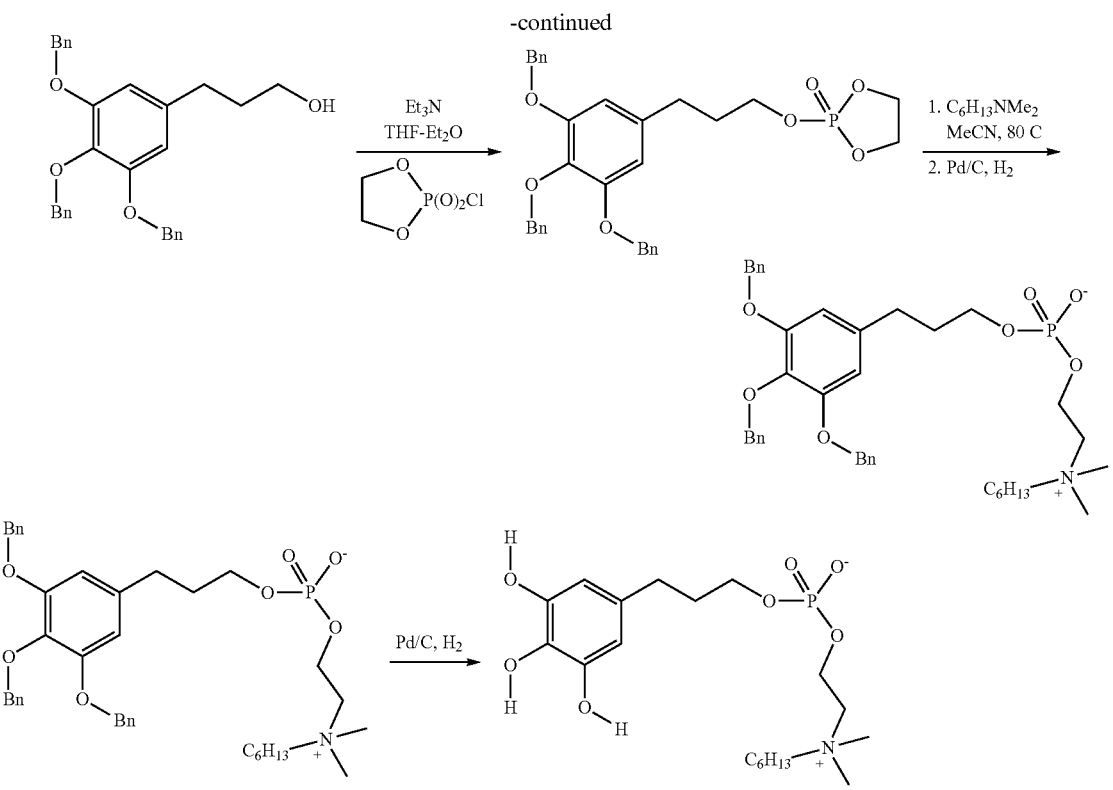

As represented in Scheme 1, the 3,4,5-trihydroxyphenyl-propionic acid may be protected by benzylation using benzyl bromide and a base such as $K_2CO_3$. Amidation of the ester using an amine, such as dimethylamine and a Grignard, such as isopropylmagnesium chloride, provides the amide. Reduction of the amide using lithium aluminum hydride provides the amine.

Alternatively, the tetrabenzyl protected ester may be reduced to the corresponding alcohol using a hydride, such as diisobutylaluminum hydride. The alcohol may be converted to the corresponding phosphate. The cyclic phosphate may be treated with an amine at elevated temperatures to provide the zwitterionic compound. The tribenzylated ether may be de-protected by hydrogenation with palladium-on-carbon.

Benzyl 3-(3,4,5-tris(benzyloxy)phenyl)propanoate:

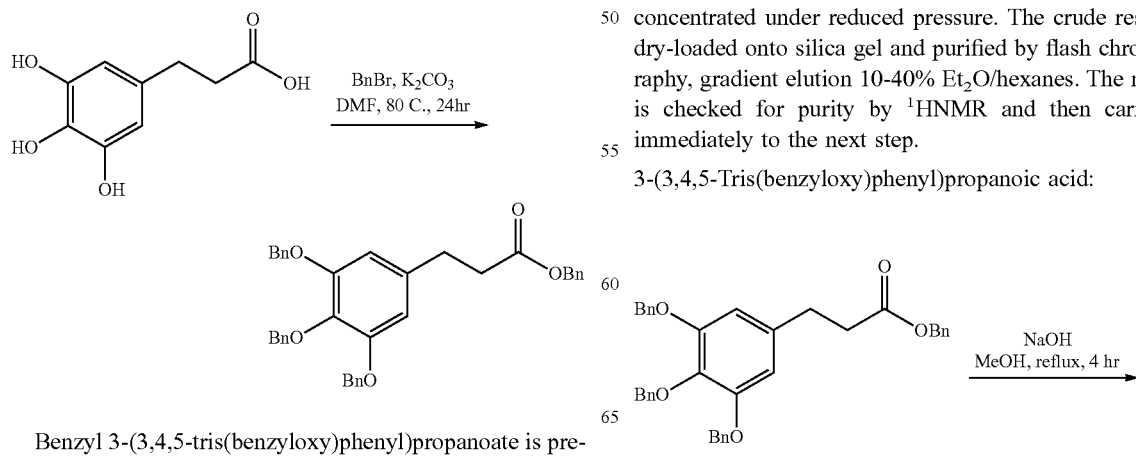

Benzyl 3-(3,4,5-tris(benzyloxy)phenyl)propanoate is prepared from the corresponding acid. A dried 500 ml 3-necked round bottom flask is fitted with rubber septa and a stir-bar and allowed to cool to ambient temperature under an argon flow. One equivalent of the acid is added, followed by 200 ml of anhydrous DMF with stirring. Once dissolved, anhydrous $K_2CO_3$ (6 equiv) is added with stirring. Fresh benzyl bromide (4.5 equiv) is added via syringe. The solution is placed in an oil bath at 80° C. and stirred for 1 day. The reaction is allowed to cool to RT, and then poured through a large fritted glass funnel into a 2 L round bottom flask to remove solids, and the reaction vessel is rinsed 3×300 ml EtOAc through the frit. The solvent is then removed with a rotary evaporator. Residual DMF is removed by 4 cycles of evaporation with toluene (500 ml). The crude residue is re-dissolved in 1.5 L of $Et_2O$ and washed 5×100 ml cold water, 1×500 ml brine, dried over anhydrous $Na_2SO_4$, and concentrated under reduced pressure. The crude residue is dry-loaded onto silica gel and purified by flash chromatography, gradient elution 10-40% $Et_2O$/hexanes. The material is checked for purity by $^1HNMR$ and then carried on immediately to the next step.

3-(3,4,5-Tris(benzyloxy)phenyl)propanoic acid:

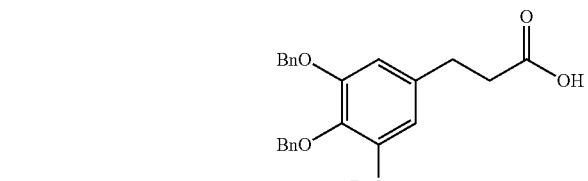

3-(3,4,5-Tris(benzyloxy)phenyl)propan-1-ol:

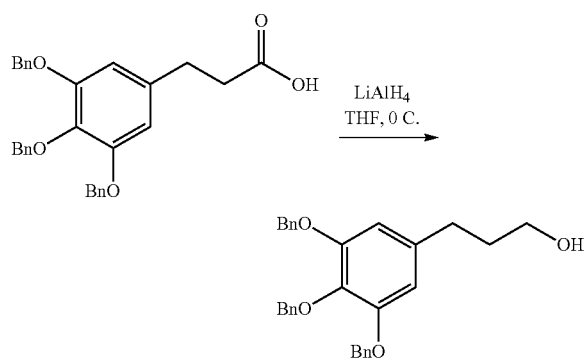

The alcohol is prepared from the acid by reduction with LiAlH$_4$. 7.24 grams of acid is dissolved in 100 ml of anhydrous THF and cooled to 0° C. Four equiv of LiAlH$_4$ are added carefully in four portions. The reaction is left to stir overnight under argon while warming to ambient temperature. The reaction is quenched according to the Fieser workup, diluted with 100 ml of Et$_2$O and the aluminum solids are filtered off. The solution is transferred to a separatory funnel, washed once with saturated NaHCO$_3$, dried over anhydrous Na$_2$SO$_4$, filtered and evaporated under reduced pressure to afford crude material. The crude material is purified on a pad of silica eluting with Et$_2$O. The compound is isolated as a clear, viscous oil.

Procedure for Preparation of Dimethylamide:

The dimethylamide is prepared with 1-1' carbonyldiimidazole as peptide coupling reagent. A dried flask is fitted with a stir bar, and a rubber septum under argon. One equiv of the corresponding carboxylic acid, 4 equiv of anhydrous Et$_3$N and anhydrous CH$_2$Cl$_2$ [0.5M] are added to the flask. The flask is cooled to 0° C. in an ice bath and stirred, and 1-1' carbonyldiimidazole (1.1 equiv) is added portion-wise. The cooling bath is removed, and the solution is stirred for 30 min while warming to RT. Dimethylamine, as the hydrochloride salt, (2 equiv), is added in one portion and the solution stirred until TLC indicated completion of the reaction. The contents are transferred to a separatory funnel, diluted with CH$_2$Cl$_2$, and the organic layer is washed 2×1N HCl, 2×sat. NaHCO$_3$ and dried over anhydrous Na$_2$SO$_4$. The organic layer is filtered, evaporated under reduced pressure, and the crude residue is filtered once over a pad of basic Al$_2$O$_3$ eluting with EtOAc, evaporated again, and purified by flash chromatography, gradient elution with 50-100% EtOAc/hexanes. The dimethylamide is obtained in high purity, by TLC.

3-(3,4,5-Tris(benzyloxy)phenyl)-N,N-dimethylpropanamide:

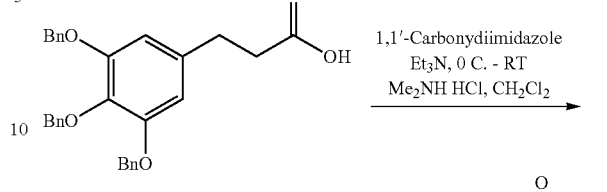

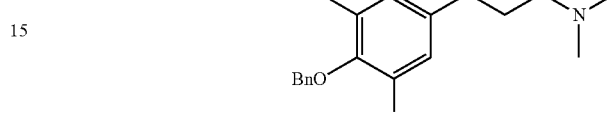

3-(3,4,5-Tris(benzyloxy)phenyl)-N,N-dimethylpropan-1-amine:

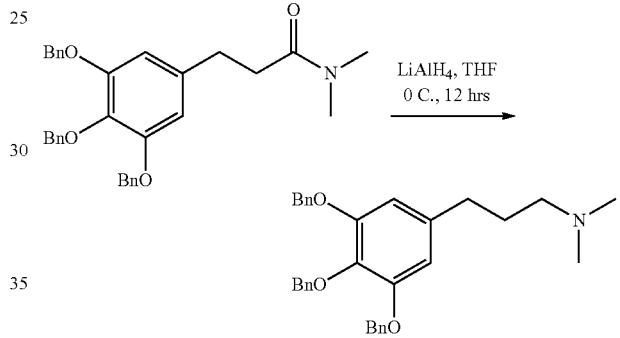

Preparation of Benzyl-Protected Compounds by the Chabrier Reaction:

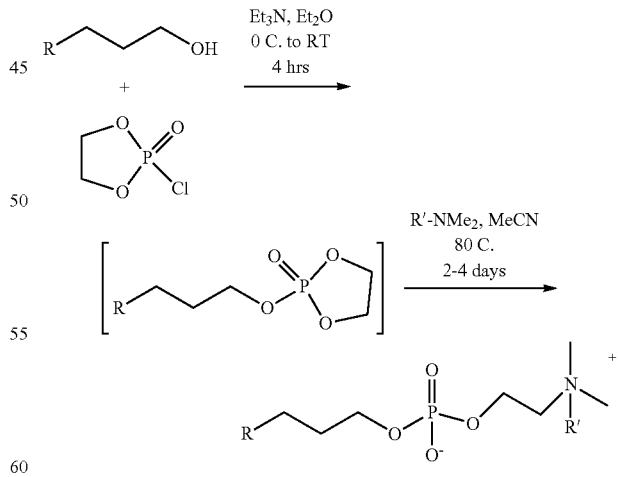

In one method, the benzyl-protected zwitterionic compounds are prepared via the Chabrier reaction, with certain modifications. Ethylene chlorophosphate (Aesar), stored in a freezer, and used as received. In a typical procedure, a flame-dried flask is fitted with a stir bar, rubber septa and cooled under positive argon. The alcohol is added to the flask followed by anhydrous Et$_2$O [0.4 M], 1.15 equiv Et$_3$N and stirred in an ice bath. 1.15 Equivalents ethylene chlorophosphate is then added dropwise via syringe where the amine hydrochloride salt precipitates, and the reaction is stirred for 10 minutes. The flask is allowed to warm to ambient temperature with stirring for 4 hours. Hexanes equal to the volume of Et$_2$O in the flask is added to precipitate the amine hydrochloride salt. The contents of the flask are filtered over a pad of basic Celite into a round bottomed flask (RBF). The contents of the reaction vessel are rinsed with hexanes, and then with Et$_2$O through the pad of basic Celite, and the solvents are removed under reduced pressure. The content is stored in the RBF under vacuum while a second reaction vessel is prepared.

A Schlenk-bomb type flask is fitted with a stir bar, flame dried, fitted with two rubber septa, under argon. The flask containing the phosphate ester is back-filled with argon, removed from the vacuum manifold, fitted with a rubber septum, and an argon needle is inserted into the septum. Anhydrous MeCN (2-4 ml per mmol alcohol) is added to this flask via syringe, and swirled until completely dissolved.

The MeCN solution containing the phosphate ester is transferred via syringe into the Schlenk flask, and the RBF is rinsed once with MeCN into the Schlenk flask. 2-4 Equiv of the amine is then added to the Schlenk flask, and the rubber septum is replaced with a Schlenk valve. The Schlenk valve is closed and the second rubber septum containing an argon needle is replaced with a glass adaptor and placed under high vacuum. The Schlenk valve is opened and the atmosphere is removed from the flask for 10 seconds. The Schlenk valve is then closed, and the flask is refluxed under vacuum with stirring for 2-4 days at 80° C. in an oil bath.

The flask is removed from the oil bath and allowed to cool to RT. The flask is then backfilled with argon, removed from the vacuum manifold and the Schlenk valve is removed. The reaction mixture is transferred via syringe into a RBF and the reaction vessel is washed 2× with CH$_2$Cl$_2$ into the RBF. Volatiles are removed under reduced pressure and residual solvents are removed by evaporation with pentanes to give the crude compound. The residue is dissolved in a minimum amount of CH$_2$Cl$_2$ and purified using C2 reverse phase silica.

Phospholane Intermediate:

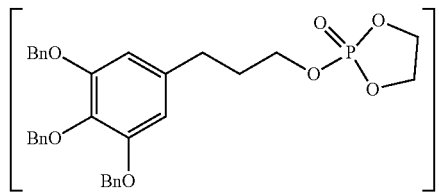

The cyclic phosphate intermediate is used immediately after preparation without further purification.

General Procedure for the Deprotection of Benzylic Ethers by Hydrogenolysis:

The oxidative stability of each of the zwitterionic compounds containing unprotected alcohols (di-ols, tri-ols, tetra-ols and penta-ols), may be either in the solid state, a solution in d$_6$-DMSO, or as a colloidal dispersion in water. Effort is made to exclude atmospheric oxygen during all manipulations after the alcohols had been deprotected. As purification of unprotected alcohols may be difficult and require application of purification techniques under inert atmosphere, effort is made to increase the purity of the intermediates immediately preceding the de-protection step and the final products are all obtained in satisfactory purity as determined by FTIR, $^1$H- and $^{13}$C-NMR Spectroscopy.

A Schlenk-type flask is fitted with stir bar, fitted with two rubber septa. 10-20 wt % of Pd/C (5% Pd, Aesar) relative to mass of substrate is added to the flask. A small quantity of CH$_2$Cl$_2$ (4-8 ml) is added via syringe. A separate RBF containing the desired amount of substrate is fitted with a rubber septum and argon needle to purge air out. The appropriate volume of a 1:1 v/v mixture of CH$_2$Cl$_2$/MeOH is added via syringe. The flask is then swirled until the benzyl-protected compound is dissolved, and the solution containing the substrate is transferred via syringe to the Schlenk flask. The RBF is rinsed with MeOH (4-8 ml), and transferred via syringe to the Schlenk flask. The Schlenk valve is then opened placing the contents of the flask under vacuum and the atmosphere is removed under vacuum. The Schlenk valve is closed, the antechamber before the valve is backfilled with argon and the glass adaptor is replaced with a rubber septum. A hydrogen balloon (double ballooned) connected to a needle is placed through the septum and then a vent needle is placed though the septum to purge argon from the antechamber for 30 seconds, and then it is removed. The Schlenk valve is opened slowly to allow hydrogen into the reaction vessel and stirring is continued for 2-4 days, with periodic replacement of the hydrogen using fresh balloons with every replacement.

Once the reaction is completed, the Schlenk valve is closed, and the remaining septum is replaced with a vacuum adaptor connected to a vacuum manifold and the antechamber before the Schlenk valve is placed under vacuum. The Schlenk valve is then opened placing the contents of the flask under vacuum and hydrogen gas is removed from the system in this manner for 5-10 minutes. A separate round bottom flask, fitted with a rubber septum, tared, and placed under positive argon flow. The Schlenk flask is then backfilled with argon, and while under positive argon flow the Schlenk valve is removed and replaced with a rubber septum. A 30 ml, Luer lock, PTFE coated syringe is fitted with a long metal needle, and the syringe is filled and purged with argon 3×, then it is inserted through the septum of the reaction vessel. The Pd/C is then separated from the reaction mixture.

Compounds are all characterized by FTIR (cm$^{-1}$), $^{13}$C NMR (125 MHz, d$_6$-DMSO) δ (ppm), $^1$H NMR (600 MHz, d$_6$-DMSO) δ (ppm) and HRMS, which confirms that the anticipated products are produced in satisfactory purity. The benzyl-protected coacervates are sufficiently stable for ESI-HRMS (QTOF2 Tandem Mass Spectrometer) and are fully characterized before hydrogenolysis.

A

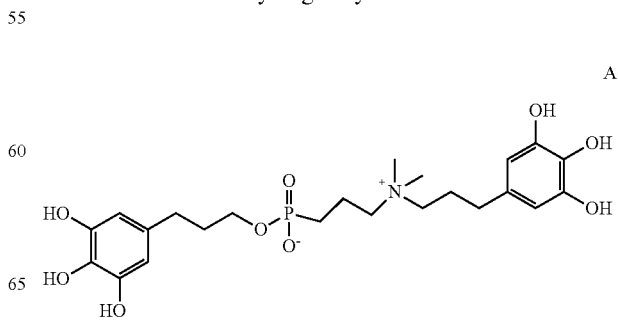

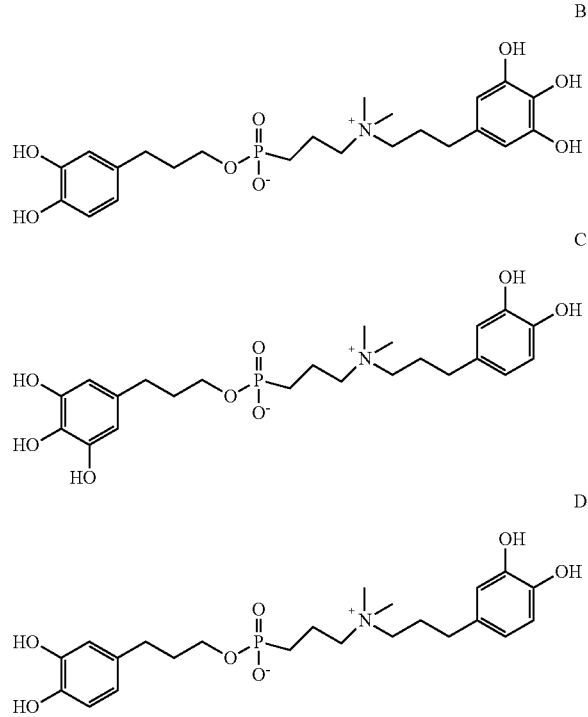

Hydrogenolysis or debenzylation of some of the protected hydroxy compounds is performed with a slightly higher catalyst loading (20 wt % of Pd/C relative to mass of starting material) and extended reaction time (more than 2 days) for complete deprotection, affording the compounds in greater than 50% yield. The corresponding 3,4-dihydroxy analogs B, C and D shown above was prepared in the similar manner.

AFM images of the primer are obtained at different concentrations: 0.001 mM (below its CAC), 0.05 mM (above CAC) and 5 mM. In one example of the primer, the 5 mM concentration shows a molecularly smooth surface suggesting consistent chemical formulation.

SFA measurements are performed on molecules deposited at 0.5 mM concentration in DI water to test the effect of concentration on the interfacial cohesive forces between the thin films. A representative compound of the present application forms monolayer (1 nm). The representative force vs. distance plots between mica surfaces of 0.5 mM aqueous dispersions of the compound is recorded. The cohesive interaction energy, $W_c$, of all molecules do not change for contact times, $t_c$ from 2 min to 12 h. The forces are measured during approach and separation of the surfaces respectively. The interaction energy of a representative compound (about 220 mJ m$^{-2}$) is high at 0.5 mM concentration.

The hard-wall thickness (the sum of the hydrodynamic diameters of the films on the upper and lower mica surfaces in SFA) of a representative compound is also measured as the limiting distance between the mica surfaces during the approach run in the SFA. SFA experiments are performed for the compounds at C=0.001 and 0.005 mM, to test the effect of deposition concentrations below the critical aggregation concentration (CAC) on the measured interaction forces, including adhesive and cohesive forces.

Atomic Force Microscopy (AFM) scans of a mica surface adsorbed with a compound of the present application from a solution in DI water of varying concentrations (5 mM). The compound forms a defect free atomically smooth bilayer on mica. No formation of small aggregates on the surface or thick multilayer is observed.

Surface Coating with Primer Compositions:

Deposition on Substrates for Medical and Dental Applications:

The surface coating, priming or deposition of the compound of the present application may be performed using standard methods known in the art, with the exception of the particular improved procedures and formulations developed and disclosed herein. For dental and medical applications, the primer may be provided in a solvent, such as water, ethanol or a mixture of a solution of water and ethanol. For dental applications, the same solvent or different solvent may be used to wash the surface of the tooth or enamel. In certain application, the solvent is water and the process provides an environmentally friendly and effective process.

In certain dental applications, washing or rinsing is not required. For example, when a low concentration solution of <0.1 wt % of catecholic methacrylate and <30 wt % of phosphomethacrylate in acetone is employed, the solution applied on a dental surface, such as tooth enamel using a micro-brush or Q-tip, the solvent (acetone) was evaporated in 2-3 seconds. At the low concentration, most molecules bind to the tooth surface (no excess remains), the rinsing or washing step was not required. In certain cases that are used on metal and ceramic surfaces, a basic buffer was applied then rinsed with water. As an example, after a few seconds of natural air drying after applying the low concentration primer solution, a primer layer formed on the tooth surface and then a dental adhesive (or dental resin) was applied, followed by a radical polymerization of methacarylate groups.

In one application, the solution employed may be used at a neutral pH, or may be maintained in acidic conditions, at a pH<7, pH 6 or pH 5. The pH may be adjusted using an acid, such as hydrochloric acid, phosphoric acid, acetic acid, sulfonic acid, phosphoacrylates or phosphomethacrylates. Depending on the type of application or the type of compound/primer employed, the pH of the solution may be above pH 5, above pH 6, above pH 6.5 or above pH 7. The solution may be dewatered or degassed using an inert gas or using vacuum or a combination thereof, and the solution and container with the solution may be flushed with an inert gas, such as nitrogen or argon as desired.

Depending on the particular application, the concentration of the primer in the solution may be prepared at different concentrations, such as a 0.0001 wt. % to 10 wt. %, about 0.001 wt. % to 10 wt. %, about 0.01 wt. % to 10 wt. %, about 0.1 wt. % to 10 wt. % or at about 0.1 wt. % to 5 wt. %; at 0.0001 wt %, 0.001 wt. %, 0.01 wt % or at 0.1 wt %, in a solvent or solvent mixture. Ethanol, water, ethanol/water, acetone, dichloromethane or other FDA approved solvents or solvent mixtures may be used for dental and medical applications. In one variation, the solvent is acetone, water or a mixture of water and an organic solvent, such as acetone, methanol or ethanol.

The bonding or binding of the adhesives of the compound of the Formula I or Formula II comprising acrylates or methacrylates and related groups on a substrate may be performed using standard methods known in the art. For example, binding may be initiated by photochemical, such as visible-light-initiated free radical polymerization, and may comprise a photoinitiator such as a visible light photoinitiator, such as camphorquinone (CQ), for example, about 0.25 wt %, and another acrylate (as co-initiator), such as 2-dimethylaminoethyl methacrylate (DMAEMA), such as at about 1 wt %.

In one variation of the combination, the combination is a mixture of catecholic methacrylate primers at 0.01-1 w/v %, and phosphomethacrylate primers at 0.1-30 w/v %, in acetone or other solvents. In one variation, the catecholic primers include catechol acrylates and methacrylates derived from eugenol and dopamine; phospho primers include MDP primer (10-methacryloyloxydecyl dihydrogen phosphate). In representative experiments, 0.01, 0.05, 0.1 or 1 w/v % of catecholic methacrylate primers were mixed with 0.1, 1, 10, 15, 20, 30 or 40 w/v % of phosphor methacrylate primers in a solvent, such as acetone, ethanol, methanol, water or mixtures thereof. The mixtures were applied onto tooth enamel, dentine, steel (stainless steel, titania, alumina) or ceramic (zirconia, porcelain, polycrystalline alumina) surfaces. The solvent in the mixture solution was evaporated in about 5 seconds, and then the primer mixtures formed a thin layer. The dental monomer adhesives or adhesives with an object were then applied or placed over the primer layer on the surface.

As a representative example of dental adhesive, Bis-GMA (20 g) and TEGMA (20 g, 18.2 mL) were added to a 100 mL flask. Because Bis-GMA is very viscous, a heat gun was used to heat the mixture and a homogeneous mixture of Bis-GMA and TEGDMA was obtained. An aliquot (8.8 mL) of the mixture was taken to a 20 mL vial. DMAEMA (71 µL) and CQ (33 mg) were added to the vial and blended with aid of sonication.

The present biomimetic dental adhesive approaches provide a durable dental bonding to maintain native dental tissues with which a new generation of dental restorations. This durable bonding is essential to preserve remaining part of natural dental tissues.

In current dental restoration and orthodontic techniques, acid etching is essential for stronger bonding via mechanical interlocking. However, etching causes damage to tooth surfaces. A two-step bonding process involving the use of a self-etching primer and then an adhesive is known in the art. That is, a typical self-etch mixture includes an acidic monomer, a co-monomer, a cross-linker, an initiator usually w/ catalyst, and various other additives. However, the two step bonding process provides a much lower bonding performance than the traditional three step process involving a separate acid etching process, applying a primer and then adding an adhesive. Typically, the multipurpose acidic monomer is usually a methacrylate functionalized with a phosphate, phosphonate, sulfinate or carboxylate group and a spacer. As disclosed herein, the method provides a non-etching process where the mixture of bioinspired catecholic monomers and an acid monomer may be used; thus, total acid strength becomes much weaker, and no damage on native tooth surfaces; or any minor damage on tooth surfaces that are naturally recovered by remineralization. By employing primers having catechol functional groups, the bonding strength and durability are significantly improved, and the process does not require an etching process or self etching with strong acidity. As disclosed herein, the bonding strength obtained on both tooth enamel and dentin surfaces is almost doubled using the mixture of the acidic primer, such as phosphomethacrylate and catecholic primers compared to the conventional two-step acid primers.

The present methods provide strong wet adhesion and bonding durability between enamel/dentin and the conventional PMA-based dental restorative adhesives. As an example, eugenol (4-allylcatechol-2-methyl ether; essential oil that has been widely used in temporary restorations) derivatives are prepared. A simple three step synthetic protocol of catechol acrylates and methacrylates from eugenol were prepared. In addition, various zwitterionic, cationic (amine), and anionic (phosphate) groups were also tethered with various phenol derivatives to form catechol methacrylate primers. The self-assembly and coupling conditions of the compounds disclosed herein are then employed in the process. The durability of bonding of the bioinspired primers related to adhesion was confirmed by ISO standard methods for dental adhesion tests.

The disclose process provides compositions with relatively strong interactions or strong bonding between tooth and dental restorative materials and resins. The primers compositions of Formulae I and II were spread thinly on a surface, such as a tooth, metal or mineral surfaces, as a primer or a primary adhesive layer; and the dental adhesives were then applied. The primary layer and the dental adhesive layer on a tooth were then cured using a dental curing light (visible blue light). Healthy 3rd molars stored in 0.1% thymol solution were used for the test. The tooth specimens were soaked in DI water for 24 hours and the surface was lightly wiped with Kimwipes before each test.

In one embodiment, the non-etching process using the disclosed compositions provided strong bonding performance, such as using a mixture of catecholic methacrylate primers at 0.01-1 w/v %, and phosphomethacrylate primers at 0.1-30 w/v %, in acetone or other solvents as disclosed herein. This process exhibited a higher bonding strength compared to the conventional acid etching or self-etching process. Catecholic primers include acrylates and methacrylates derived from eugenol (see Ahn, B. K., et al. (2014). "Surface-initiated self-healing of polymers in aqueous media." *Nat Mater* 13(9): 867-872); phospho primers includes MDP primer (10-methacryloyloxydecyl dihydrogen phosphate). In representative experiments, 0.01, 0.05, 0.1 or 1 w/v % of catecholic methacrylate primers were mixed with 0.1, 1, 10, 15, 20, 30 or 40 w/v % of phosphor methacrylate primers in a solvent, such as acetone, ethanol or methanol or mixtures thereof. The mixtures were applied on to tooth enamel, dentine, steel (stainless steel, titania, alumina) or ceramic surfaces (zirconia, porcelain, polycrystalline alumina). The solvent in the mixture solution was evaporated in about 5 seconds, and then the primer mixtures formed a thin layer. The dental adhesive was then applied on the bottom of an object or over the primer layer on the surface. The object was then placed over the primer/adhesive layer, followed by visible light curing for 20 seconds to several minutes as needed. The shear bonding strength was then measured for each sample. In these experimental conditions, the mixtures with 0.01-0.1% of the catecholic methacrylate and 10-30% of the phosphomethacrylate showed the highest bonding performance. This catecholic non-etching process provides much stronger (up to 5 times) bonding strength than conventional dental restoration processes, which include acidic self-etching primers/monomers or a 10-30 second acid etching step. The resulting compositions provide significantly improved performance in the shear bonding test on various surfaces including tooth enamel, tooth dentine, stainless steel, alumina, titania, zirconia, glass, and other minerals, ceramics and metals. As it is known, the acid etching leads to damage of native enamel and dentin tissues, resulting in potential dental hypersensitivity, caries, re-restoration and eventual tooth loss.

As disclosed herein, the compositions comprising a mixture of the acrylates, such as the catecholic methacrylate and the phospho methacrylate, may comprise of about 0.01-0.05%, 0.05-0.75%, 0.05-0.1% or about 0.1-0.2% of the catecholic methacrylate, in a mixture with about 5%, 10%, 15%, 20%, 25% and about 30% of the phospho methacrylate, depending on the structure of the acrylates as disclosed herein.

It is noted that exposed collagen fibrils can be affected by the dentin matrix metalloproteinases (MMPs) inducing hydrolytic degradation, which might result in reduced bond strength. Most MMPs are synthesized and released from odontoblasts in the form of proenzymes, requiring activation to degrade extracellular matrix components. However, they can be activated by modem self-etch and etch-and-rinse adhesives. Therefore, eliminating the modern etching process provides a significant innovation in the dental restoration process. The combination of the two functional groups, for example, a phospho-group and a catechol group, or an addition of other functional groups such as amine provide a further increase shear bonding strength and durability of the dental adhesives. In addition, the strong and durable priming layer may also protect the collagenous tissues from denaturation after acid etching treatment. Alternatively, the etching step may be eliminated using the present method.

Representative Deposition Procedure:

In one embodiment, the application of the present adhesive may be made in a variation of the above method. In one variation, the surface is cleaned and wiped using a gauze, a Kimwipe, or a clean towel; for example, tooth surfaces are cleaned with pumice and dried with air flow and/or wiped with a Kimwipe to remove water on the surfaces. On to the clean and dry tooth surface a primer composition comprising the desired adhesive primer formulation is then applied as a solution or gel. The formulation may be brushed with a microbrush or a Q-tip, or applied with a squeeze bottle or eye dropper bottle, and the formulation is spread, the tooth surface is then dried (in case of acetone, allowing the solvent to dry in a few seconds) to create the desired surface or area for the dental adhesive or composite application for the desired period of time. Depending on the nature of the adhesive primers and the amount applied onto the surface, the formulation is applied over a period of a few seconds, such as about 10 second, 5 seconds, 3 seconds or less. A dental resin composite or a dental adhesive is then applied over the primer formulation as desired. The photo-sensitive adhesive may be applied to the dental appliance, optionally with a primer, and the dental appliance may be mounted onto the tooth surface and held for a period of time until the appliance remains firmly on the tooth surface.

Deposition on Substrates for Materials and Electronics Applications:

In one embodiment, the primer solution may be applied onto a surface, such as a mineral and/or metal oxide surface, for a period of time to allow the compound/primer to set up or otherwise adsorbed or adhere to the surface. Depending on the nature of the surface and the structure of the compound, adhesion of the compound to the surface may take less than about 60 minutes, less than 30 minutes, less than 15 minutes, less than 10 minutes, less than 5 minutes, less than 3 minutes, less than 1 minutes or less than a few seconds. Once the primer is adsorbed to the surface, any excess primer may be removed from the surface by rising with a solvent or solvent mixture. In case of concentration of the solution is low such as <0.1 w/v % of catecholic primers, the rinsing is not required because there is no excess of catecholic primers that can inhibit radical polymerization. For certain applications, the solvent or solvent mixture may be water, ethanol, methanol, acetone, dichloromethane, ether, or a mixture of two or more solution. Depending on the desired application, the surface with the adsorbed primer may be dried using air, heat, wiping or a combination thereof until the desired dryness is achieved. In case the surfaces are metal oxides, basic buffer (e.g., pH 10 buffer) or basic solution with a high ionic strength applied on to the primed surfaces or prior to the priming step to form coordination bonds between ligand groups such as catechol and metal on the surfaces. Subsequently, the basic buffer or solution was rinsed with water and dried. Adhesives or resin composites are then applied over the treated surfaces.

The solvent or solvent mixture employed in the primer solution and/or as a washing solvent may include water, acetone, methanol, ethanol, propanol, isopropanol, acetone, methylethyl ketone, hexane, cyclohexane, heptane, dichloromethane, ether, toluene, xylenes, THF, Me-THF (2-Me-THF), and N-methylpyrrolidone; and various mixtures thereof. In certain aspects, the solvent is water or ethanol, or a mixture of the solvents with water, and the process provides an environmentally friendly and effective process.

The thickness of the adhered/adsorbed layer may be about 0.5-50 nm, 0.1-40 nm, 0.1-30 nm, 0.1-20 nm, 0.1-10 nm, 0.1-5 nm or 0.1-3 nm, about 1-10 nm; or about 1 to 3 mm. For deposition of the solution comprising the compound/primer of the present application, the thickness will depend on the nature of the compound and the desired thickness of the layer and the nature of the application. For the preparation of SAMs, the thickness of the adhered/adsorbed layer may be less than for other self-assembled layers with the desired thickness. Optionally, the surface comprising a first layer may be completely dried before applying second layer or subsequent layers that may be the same or different, and may be a self-assembled layer or SAM.

For other materials or electronic applications, the primer may be provided in a solvent, such as water, ethanol or a mixture of a solution of water and ethanol; or the solvent or solvent mixture employed in the primer solution and/or as a washing solvent may include methanol, ethanol, propanol, isopropanol, acetone, dichloromethane, methylethyl ketone, hexane, cyclohexane, heptane, toluene, xylenes, THF, Me-THF and N-methylpyrrolidone, and various mixtures thereof. In one variation, the same solvent or different solvent may be used to wash the surface of the substrate. In one variation, the solvent is water, acetone, ethanol or a mixture of the solvents.

In one application, the primer solution employed may be used at a neutral pH, or may be maintained in acidic conditions, at a pH<7, pH<6 or pH<5. The pH may be adjusted using an acid, such as phosphoric acid, acetic acid or sulfonic acid, or phospho-, acetic-, or surf-primers, such as 10-methacryloyloxydecyl dihydrogen phosphate. Depending on the type of application or the type of compound/primer employed, the pH of the solution may be pH>5, pH>6, pH>6.5 or pH>7. The solution may be dewatered or degassed using an inert gas or using vacuum or a combination thereof, and the solution and container with the solution may be flushed with an inert gas, such as nitrogen or argon as desired.

Depending on the particular application, the concentration of the primer in the solution may be prepared at different concentrations, such as a 0.0001 wt. % to 10 wt. %, about 0.001 wt. % to 10 wt. %, about 0.01 wt. % to 10 wt. %, about 0.1 wt. % to 10 wt. % or at about 0.1 wt. % to 5 wt. %; at 0.0001 wt. %, 0.001 wt. %, 0.01 wt. % or at 0.1 wt. %, in a solvent or solvent mixture.

In one aspect, the disclosed primers may be formulated with conventional primers before uses. For example, catechol-SP-acrylates (or methacrylates) may be mixed with a phospho-SP-acrylates (or methacrylates) or a silane-SP-acrylate (or methacrylates), or mixtures thereof.

In one embodiment, the solution may be applied onto a surface, such as a metal or metal oxide surface for a period of time to allow the compound/primer to set up or otherwise adsorbed or adhere to the surface. Depending on the nature of the surface and the structure of the compound, adhesion of the compound to the surface may take less than about 60 minutes, less than 30 minutes, less than 10 minutes, less than 5 minutes, less than 3 minutes, less than 2 minutes or less than about 1 minute. The short adhesion time for depositing the compound of the present application permits the rapid deposition and fabrication of electronic devices such as nano-electronic devices.

Once the primer is adsorbed to the surface, any excess primer may be removed from the surface by washing or rising with a solvent or solvent mixture. Depending on the desired application, the surface with the adsorbed primer may be dried using air, heat or a combination thereof until the desired dryness is achieved.

The thickness of the adhered/adsorbed layer may be about 0.5-50 nm, 0.1-40 nm, 0.1-30 nm, 0.1-20 nm, 0.1-10 nm, 0.1-5 nm, 0.1-3 nm or 0.1-2 nm; or about 1-3 mm or less. For deposition of the solution comprising the compound/primer of the present application, the thickness will depend on the nature of the compound and the desired application. For the preparation of SAMs, the thickness of the adhered/adsorbed layer may be less than for other self-assembled layers with the desired thickness. Optionally, the surface comprising the layer may be completely dried before applying second layer or subsequent layers.

A mixture of catechol-SP-methacrylate and 10-methacryloyloxydecyl dihydrogen phosphate (ratio from 0.01 to 0.99 to 0.99 to 0.01) was prepared in acetone (0.01 to 10 w/v %). The mixture was applied on tooth surface using a microbrush for 2-3 seconds and acetone evaporated in 2-3 seconds. A self-assembled layer was then formed on tooth surfaces. Catechol and phospho groups bind to a tooth surface and superficial methacrylate groups remained unbound. Methacrylic dental resins were applied on the top of the self-assembled layer. When curing occurred by a radical polymerization, unbound methacrylate groups of the primers crosslinked with methacrylate groups of dental resins. As a result, the primer mixture of SP-methacrylate and 10-methacryloyloxydecyl dihydrogen phosphate bridged between tooth and dental resin, and bonding strength of dental resin increased significantly compared to catechol-SP-methacrylate itself and 10-methacryloyloxydecyl dihydrogen phosphate itself, respectively.

Applications for Adhesive, Composites and Cement:

The treatment of adhesives, coating compositions, composites, paint and sealants with the primer or compounds of the present application is substantially similar to the methods described above, with standard procedural modifications known in the art for the treatment of such materials, and applying the advantages of the methods and compositions disclosed herein. For applying the method to fillers, for example, the mineral and/or metal oxide fillers (powders, fibers etc. . . . ) are treated with the primer solution.

Fillers, such as pure fillers required as different compositions for different applications, are added to a primer solution. The solution is vigorously stirred and or sonicated for several minutes at about RT. The fillers are removed or isolated from the solvent, and are rinsed with a solvent or solvent mixture, and then filtered or isolated by centrifugation. Depending on the nature of the composition and the desired application, the fillers may be washed and rinsed more than once as needed. The fillers are then dried, such as by air blowing (for dental applications, for example), or may be dried by a freeze dried procedure, or dried by hot air, room temperature air or gas, or dried by vacuum, as known in the art to the desired level of dryness.

In one particular embodiment, the dried fillers may be added to various different materials, such as a monomer, a co-monomer mixture, pre-polymer and polymer for performing a polymerizing process with the fillers. In another embodiment as is known in the art, the fillers may be added to a pre-cement matrix or adhesive for preparing an adhesive. In another embodiment, the fillers may be combined with a coating, a paint composition, a rubber or plastic, an ink and/or sealant before the composition is cured and/or dried. Employing the processes described herein, the mechanical properties (including the hardness, thickness etc. . . . ) of the composite material (with the fillers) may be significantly increased or improved.

Representative compounds of the Formula I that may be prepared according to the present disclosure are provided in the Table:

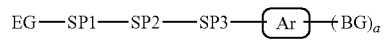

TABLE

| Compound No. | EG— | —SP1—SP2—SP3— | —Ar—(BG)$_a$ |
|---|---|---|---|
| 1 | —OH | —(CH$_2$)$_6$—NHC(O)—(CH$_2$CH$_2$O)$_2$—(CH$_2$)$_6$— | 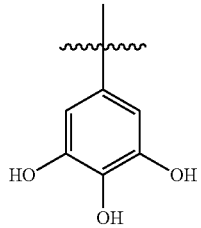 [SMILES: *c1cc(O)c(O)c(O)c1] |

TABLE-continued

| Compound No. | EG— | —SP1—SP2—SP3— | —Ar—(BG)$_a$ |
|---|---|---|---|
| 2 | —OH | —(CH$_2$)$_6$—NHC(O)—(CH$_2$CH$_2$O)$_2$—(CH$_2$)$_6$— | 3,4-dihydroxyphenyl |
| 3 | —OH | —(CH$_2$)$_6$—NHC(O)—(CH$_2$CH$_2$O)$_2$—(CH$_2$)$_6$— | 2,3,4-trihydroxyphenyl |
| 4 | —OH | —(CH$_2$)$_6$—NHC(O)—(CH$_2$CH$_2$O)$_2$—(CH$_2$)$_6$— | 3-(SiH$_2$OH)-4,5-dihydroxyphenyl |
| 5 | —OH | —(CH$_2$CH$_2$O)$_3$CH$_2$CH$_2$—CONCH$_3$—(CH$_2$CH$_2$O)$_3$CH$_2$CH$_2$— | 3,4,5-trihydroxyphenyl |
| 6 | —OH | —(CH$_2$CH$_2$O)$_3$CH$_2$CH$_2$—CONCH$_3$—(CH$_2$CH$_2$O)$_3$CH$_2$CH$_2$— | 3,5-dihydroxy-4-(SiH$_2$OH)phenyl |
| 7 | —OH | —(CH$_2$)$_6$—OPO$_3^-$(CH$_2$)$_2$—N$^+$(CH$_3$)$_2$—(CH$_2$)$_6$— | 3,5-dihydroxy-4-(SiH$_2$OH)phenyl |

TABLE-continued

| Compound No. | EG— | —SP1—SP2—SP3— | —Ar—(BG)$_a$ |
|---|---|---|---|
| 8 | —OH | —(CH$_2$)$_6$—OPO$_3^-$(CH$_2$)$_2$—N$^+$(CH$_3$)$_2$—(CH$_2$)$_6$— | 2,3,4-trihydroxyphenyl |
| 9 | —OH | —(CH$_2$)$_6$—OPO$_3^-$(CH$_2$)$_2$—N$^+$(CH$_3$)$_2$—(CH$_2$)$_6$— | 3-(SiH$_2$OH)-4,5-dihydroxyphenyl (with OH) |
| 10 | —OH | —(CH$_2$)$_6$—OPO$_3^-$(CH$_2$)$_2$—N$^+$(CH$_3$)$_2$—(CH$_2$)$_6$— | 3,4,5-trihydroxyphenyl |
| 11 | —SiMe$_2$OH | —(CH$_2$)$_6$—NHC(O)—(CH$_2$CH$_2$O)$_2$—(CH$_2$)$_6$— | 3,4,5-trihydroxyphenyl |
| 12 | —SiMe$_2$OH | —(CH$_2$)$_6$—NHC(O)—(CH$_2$CH$_2$O)$_2$—(CH$_2$)$_6$— | 2,3,4-trihydroxyphenyl |
| 13 | —SiMe$_2$OH | —(CH$_2$)$_6$—NHC(O)—(CH$_2$CH$_2$O)$_2$—(CH$_2$)$_6$— | 3-(SiH$_2$OH)-4,5-dihydroxyphenyl (with OH) |

TABLE-continued

| Compound No. | EG— | —SP1—SP2—SP3— | —Ar—(BG)$_a$ |
|---|---|---|---|
| 14 | —SiMe$_2$OH | —(CH$_2$)$_6$—OPO$_3^-$(CH$_2$)$_2$—N$^+$(CH$_3$)$_2$—(CH$_2$)$_6$— | 3,5-dihydroxyphenyl with SiH$_2$OH at 4-position |
| 15 | —SiMe$_2$OH | —(CH$_2$)$_6$—OPO$_3^-$(CH$_2$)$_2$—N$^+$(CH$_3$)$_2$—(CH$_2$)$_6$— | 3,4,5-trihydroxyphenyl |
| 16 | —SiMe$_2$OH | —(CH$_2$)$_6$—OPO$_3^-$(CH$_2$)$_2$—N$^+$(CH$_3$)$_2$—(CH$_2$)$_6$— | 3,4-dihydroxyphenyl with HOH$_2$Si at 5-position |
| 17 | C$_6$alkyl | —(CH$_2$)$_6$—NHC(O)—(CH$_2$CH$_2$O)$_2$—(CH$_2$)$_6$— | 3,5-dihydroxyphenyl with OH at 4-position |
| 18 | C$_6$alkyl | —(CH$_2$)$_6$—NHC(O)—(CH$_2$CH$_2$O)$_2$—(CH$_2$)$_6$— | 3,4-dihydroxyphenyl with HOH$_2$Si at 5-position |
| 19 | C$_6$alkyl | —(CH$_2$)$_6$—NHC(O)—(CH$_2$CH$_2$O)$_2$—(CH$_2$)$_6$— | 3,5-dihydroxyphenyl with SiH$_2$OH at 4-position |

TABLE-continued

| Compound No. | EG— | —SP1—SP2—SP3— | —Ar—(BG)$_a$ |
|---|---|---|---|
| 20 | C$_6$alkyl | —(CH$_2$)$_6$—OPO$_3^-$(CH$_2$)$_2$—N$^+$(CH$_3$)$_2$—(CH$_2$)$_6$— | 3,4,5-trihydroxyphenyl |
| 21 | C$_6$alkyl | —(CH$_2$)$_6$—OPO$_3^-$(CH$_2$)$_2$—N$^+$(CH$_3$)$_2$—(CH$_2$)$_6$— | 3-(SiH$_2$OH)-4,5-dihydroxyphenyl (with HOH$_2$Si substituent) |
| 22 | —CF$_3$ | —(CH$_2$)$_6$—NHC(O)—(CH$_2$CH$_2$O)$_2$—(CH$_2$)$_6$— | 3,4,5-trihydroxyphenyl |
| 23 | —CF$_3$ | —(CH$_2$)$_6$—NHC(O)—(CH$_2$CH$_2$O)$_2$—(CH$_2$)$_6$— | 2,3,4-trihydroxyphenyl |
| 24 | —CF$_3$ | —(CH$_2$)$_6$—NHC(O)—(CH$_2$CH$_2$O)$_2$—(CH$_2$)$_6$— | 3-(SiH$_2$OH)-4,5-dihydroxyphenyl (with HOH$_2$Si substituent) |
| 25 | —CF$_3$ | —(CH$_2$CH$_2$O)$_3$CH$_2$CH$_2$—CONCH$_3$—(CH$_2$CH$_2$O)$_3$CH$_2$CH$_2$— | 4-(SiH$_2$OH)-3,5-dihydroxyphenyl |

TABLE-continued

| Compound No. | EG— | —SP1—SP2—SP3— | —Ar—(BG)$_a$ |
|---|---|---|---|
| 26 | —CF$_3$ | —(CH$_2$)$_6$—OPO$_3^-$(CH$_2$)$_2$—N$^+$(CH$_3$)$_2$—(CH$_2$)$_6$— | 3,5-dihydroxy-4-hydroxyphenyl (HO, OH at 3,5; OH at 4) |
| 27 | —CF$_3$ | —(CH$_2$)$_6$—OPO$_3^-$(CH$_2$)$_2$—N$^+$(CH$_3$)$_2$—(CH$_2$)$_6$— | 2,3,4-trihydroxyphenyl |
| 28 | —CF$_3$ | —(CH$_2$)$_6$—OPO$_3^-$(CH$_2$)$_2$—N$^+$(CH$_3$)$_2$—(CH$_2$)$_6$— | 3-(HOH$_2$Si)-4,5-dihydroxyphenyl with OH |
| 29 | Phenyl- | —(CH$_2$)$_6$—NHC(O)—(CH$_2$CH$_2$O)$_2$—(CH$_2$)$_6$— | 3,5-dihydroxy-4-hydroxyphenyl |
| 30 | Phenyl- | —(CH$_2$)$_6$—NHC(O)—(CH$_2$CH$_2$O)$_2$—(CH$_2$)$_6$— | 2,3,4-trihydroxyphenyl |
| 31 | Phenyl- | —(CH$_2$)$_6$—NHC(O)—(CH$_2$CH$_2$O)$_2$—(CH$_2$)$_6$— | 3-(HOH$_2$Si)-4,5-dihydroxyphenyl with OH |

TABLE-continued
| Compound No. | EG— | —SP1—SP2—SP3— | —Ar—(BG)$_a$ |
|---|---|---|---|
| 32 | Phenyl- | —(CH$_2$CH$_2$O)$_3$CH$_2$CH$_2$—CONCH$_3$—(CH$_2$CH$_2$O)$_3$CH$_2$CH$_2$— | 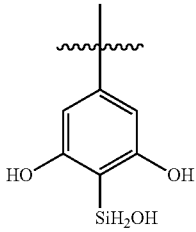 |
| 33 | Phenyl- | —(CH$_2$CH$_2$O)$_3$CH$_2$CH$_2$—CONCH$_3$—(CH$_2$CH$_2$O)$_3$CH$_2$CH$_2$— | 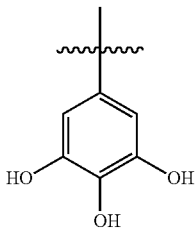 |
| 34 | Phenyl- | —(CH$_2$)$_6$—OPO$_3^-$(CH$_2$)$_2$—N$^+$(CH$_3$)$_2$—(CH$_2$)$_6$— | 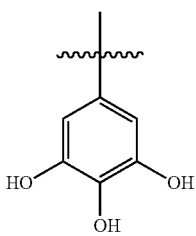 |
| 35 | Phenyl- | —(CH$_2$)$_6$—OPO$_3^-$(CH$_2$)$_2$—N$^+$(CH$_3$)$_2$—(CH$_2$)$_6$— | 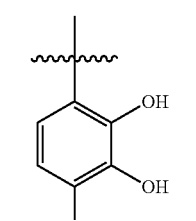 |
| 36 | Phenyl- | —(CH$_2$)$_6$—OPO$_3^-$(CH$_2$)$_2$—N$^+$(CH$_3$)$_2$—(CH$_2$)$_6$— | 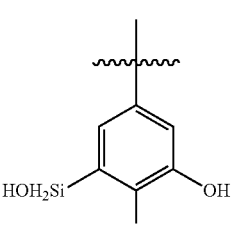 |
| 37 | C$_6$alkyl | —(CH$_2$)$_6$—NHC(O)—(CH$_2$CH$_2$O)$_2$—(CH$_2$)$_6$— | 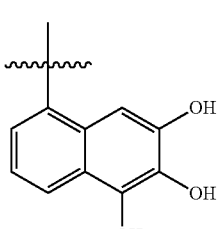 |

TABLE-continued

| Compound No. | EG— | —SP1—SP2—SP3— | —Ar—(BG)$_a$ |
|---|---|---|---|
| 38 | C$_6$alkyl | —(CH$_2$)$_6$—OPO$_3^-$(CH$_2$)$_2$—N$^+$(CH$_3$)$_2$—(CH$_2$)$_6$— | 8-substituted naphthalene-1,6-diol with 7-SiH$_2$OH |
| 39 | C$_6$alkyl | —(CH$_2$)$_6$—OPO$_3^-$(CH$_2$)$_2$—N$^+$(CH$_3$)$_2$—(CH$_2$)$_6$— | 4-substituted isoquinoline-6,7,8-triol |
| 40 | Phenyl- | —(CH$_2$)$_6$—NHC(O)—(CH$_2$CH$_2$O)$_2$—(CH$_2$)$_6$— | 4-substituted isoquinoline-6,7,8-triol |
| 41 | Phenyl- | —(CH$_2$)$_6$—NHC(O)—(CH$_2$CH$_2$O)$_2$—(CH$_2$)$_6$— | 8-substituted naphthalene-1,6-diol with 7-SiH$_2$OH |
| 42 | Phenyl- | —(CH$_2$)$_6$—OPO$_3^-$(CH$_2$)$_2$—N$^+$(CH$_3$)$_2$—(CH$_2$)$_6$— | 8-substituted naphthalene-1,6,7-triol |
| 43 | Phenyl- | —(CH$_2$CH$_2$O)$_3$CH$_2$CH$_2$—CONCH$_3$—(CH$_2$CH$_2$O)$_3$CH$_2$CH$_2$— | 4-substituted isoquinoline-6,7,8-triol |

Compounds that may be used as co-polymers may also include:
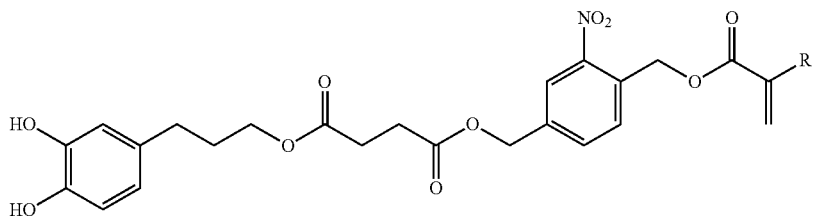
50: R = H
51: R = Me
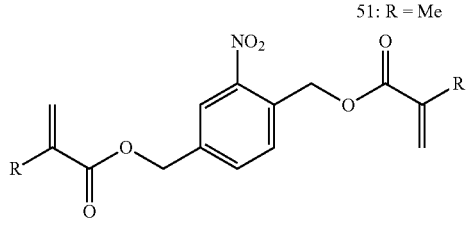
52: R = H
53: R = Me
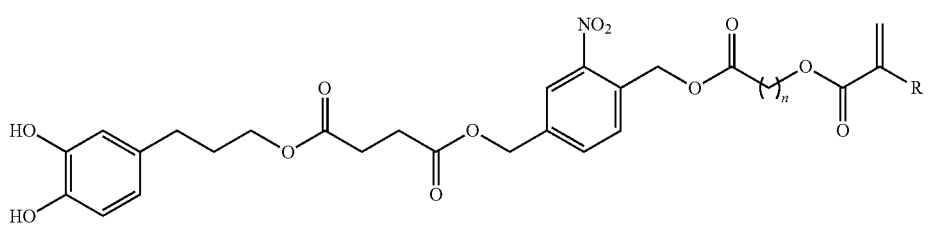
55: R = H, n = 1; 56: R = Me, n = 1
57: R = H, n = 2; 58: R = Me, n = 2
59: R = H, n = 3; 60: R = Me, n = 3
61: R = H, n = 4; 62: R = Me, n = 4
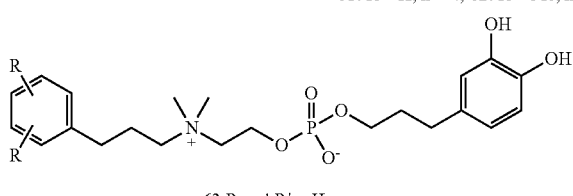
63 R and R' = H
64 R and R' = 3,4-dihydroxy
65 R and R' = 3,5-ditrifluoromethyl
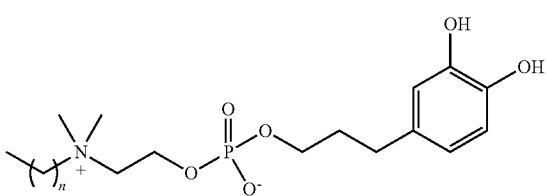
66 n = 1; 67 n = 2; 68 n = 3;
69 n = 4; 70 n = 5; 71 n = 6;
72 n = 7; 73 n = 8; 74 n = 9;
75 n = 10; 76 n = 11; 77 n = 12
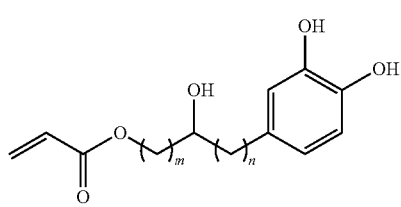
78 m and n = 1; 79 m = 1, n = 2;
80 m and n = 2; 81 m = 2, n = 3;
82 m and n = 3; 83 m = 3, n = 4;
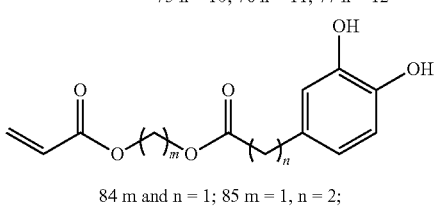
84 m and n = 1; 85 m = 1, n = 2;
86 m and n = 2; 87 m = 2, n = 3;
88 m and n = 3; 88 m = 3, n = 4
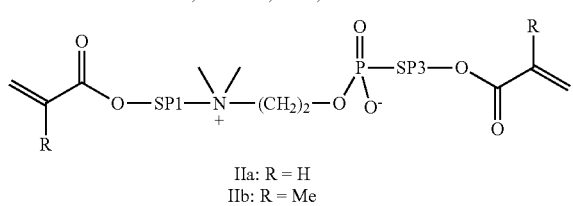
IIa: R = H
IIb: R = Me
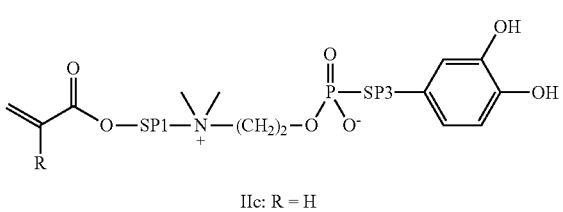
IIc: R = H
IId: R = Me

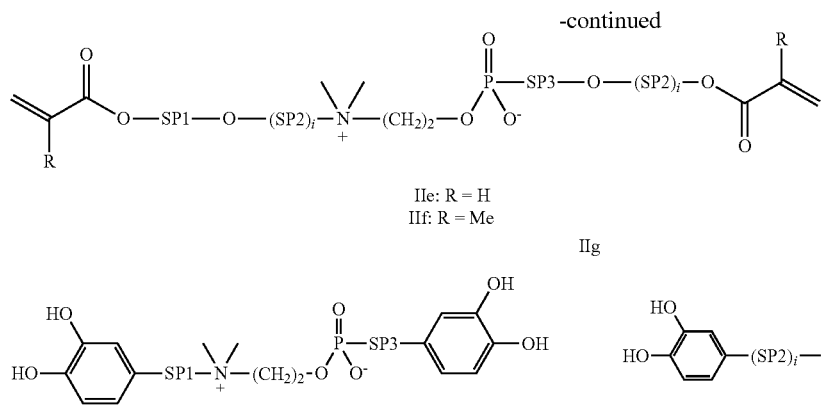

IIe: R = H
IIf: R = Me wherein i, SP1, SP2 and SP3 are as defined if Formulae I and II.

REFERENCES

1. B. K. Ahn, D. W. Lee, J. N. Israelachvili, J. H. Waite, Surface-initiated self-healing of polymers in aqueous media. *Nat Mater* 13, 867-872 (2014). 2. B. K. Ahn, S. Das, R. Linstadt, Y. Kaufman, N. R. Martinez-Rodriguez, R. Mirshafian, E. Kesselman, Y. Talmon, B. H. Lipshutz, J. N. Israelachvili, J. H. Waite, High-performance mussel-inspired adhesives of reduced complexity. *Nat Commun* 6, (2015). 3. H. Zeng, D. S. Hwang, J. N. Israelachvili, J. H. Waite, Strong reversible $Fe^{3+}$-mediated bridging between dopa-containing protein films in water. *Proceedings of the National Academy of Sciences* 107, 12850-12853 (2010). 4. H. Lee et al., Single-molecule mechanics of mussel adhesion. *Proc Natl Acad Sci USA*, 103, 12999-13003 (2006). 5. M. Krogsgaard et al. Gels and threads: Mussel-inspired one-pot route to advanced responsive materials. *Chemical Communications* 50, 13278-13281 (2014). 6. C. N. Z. Schmitt et al., Role of Sacrificial Protein-Metal Bond Exchange in Mussel Byssal Thread Self-Healing. *Biomacromolecules* 16, 2852-2861 (2015). 8. P. B. Messersmith et al., Universal Surface-Initiated Polymerization of Antifouling Zwitterionic Brushes Using a Mussel-Mimetic Peptide Initiator, *Langmuir*, 2012, 28, 7258-7266. 9. P. B. Messersmith et al., Single-molecule mechanics of mussel adhesion, PNAS, 103, No. 35, 12999-13003 (2006).

We claim:

1. A dental adhesive comprising a formulation or a mixture of:
   a) the compounds of the Formula II:

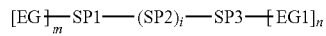

wherein:
   m is 1, 2 or 3; n is 1, 2 or 3; i is 1, 2 or 3;
   each EG and EG1 is an end group independently selected from the group consisting of a $C_{1-12}$alkyl, $CH_2$=CH—, $CH_2$=C($C_{1-3}$ alkyl)-, $CH_2$=CHC(O)—, $CH_2$=C($C_{1-3}$ alkyl)C(O)—, $CH_2$=CHC(O)O—, $CH_2$=C($C_{1-3}$ alkyl)C(O)O—, and —Ar-(BG)$_a$; and wherein, a is 2 or 3; and wherein each BG is selected from the group consisting of —OH;
   each of SP1, SP2 and SP3 is a spacer independently selected from the group consisting of —O—, —C(O)—, —C—, —CH—, —(CH$_2$)$_q$—, —(CH(OH))$_q$—, —(CH$_2$CH(OH)CH$_2$)$_q$—, —(C(CH$_3$)$_2$)$_q$—, —(CH(CH$_3$))$_q$—, —OC(O)—, —CO$_2$—, —OCH$_2$CH$_2$C(O)—, —C(O)CH$_2$CH$_2$C(O)—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$—,
   wherein p is 1-6, and q is 1-6; and
   b) a dental primer selected from the group consisting of phospho-SP-acrylates and phospho-SP-methacrylates.

2. The dental adhesive of claim 1 where the phospho-SP-methacrylates is 10-methacryloyloxydecyl dihydrogen phosphate.

3. The dental adhesive of claim 1, further comprising a photoinitiator.

4. The dental adhesive of claim 3, where photo-initiators are camphorquinone (CQ) and 2-dimethylaminoethyl methacrylate (DMAEMA).

5. The dental adhesive of claim 1 further comprising a solvent selected from the group consisting of acetone, alcohols and water, or mixtures thereof.

6. The dental adhesive of claim 1 further comprising a filler selected from the group consisting of mineral fillers, fumed silica, non-acid reactive fluoroaluminosilicate glasses fillers, quartz, ground glasses, ground polymer resins, non-water-soluble fluorides, silica gels, calcium silicate, zirconium silicate, zeolites and molecular sieves, or mixtures thereof.

7. The dental adhesive of claim 1 further comprising a dental adhesive selected from the group consisting of Bis-GMA, TEGDMA and DMAEMA.

8. The dental adhesive of claim 7, wherein the adhesive provides wet adhesion and bonding durability without acid etching or self-etching.

9. The dental adhesive of claim 1 that is an orthodontic primer, adhesive, composite or a resin.

10. The dental adhesive of claim 1, wherein the adhesive is a combination or a blend of a catechol methacrylate primer at 0.01-1 w/v % and a phosphomethacrylate primer at 0.1-30 w/v % in a solvent.

* * * * *